(12) United States Patent
Meyerson et al.

(10) Patent No.: US 11,903,746 B2
(45) Date of Patent: Feb. 20, 2024

(54) INCONTINENCE PREDICTION SYSTEMS AND METHODS

(71) Applicant: Hill-Rom Services, Inc., Batesville, IN (US)

(72) Inventors: Craig M. Meyerson, Syracuse, NY (US); Kirsten M. Emmons, Batesville, IN (US); David L. Ribble, Batesville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 332 days.

(21) Appl. No.: 17/330,481

(22) Filed: May 26, 2021

(65) Prior Publication Data

US 2021/0401380 A1 Dec. 30, 2021

Related U.S. Application Data

(60) Provisional application No. 63/043,819, filed on Jun. 25, 2020.

(51) Int. Cl.
*A61B 5/00* (2006.01)
*A61B 5/20* (2006.01)
*A61B 5/11* (2006.01)
*A61G 7/018* (2006.01)

(52) U.S. Cl.
CPC ............ *A61B 5/746* (2013.01); *A61B 5/0004* (2013.01); *A61B 5/1115* (2013.01); *A61B 5/202* (2013.01); *A61G 7/018* (2013.01); *A61G 2203/20* (2013.01)

(58) Field of Classification Search
None
See application file for complete search history.

(56) References Cited

U.S. PATENT DOCUMENTS

| | | | |
|---|---|---|---|
| 5,561,412 A | 10/1996 | Novak et al. | |
| 5,838,223 A | 11/1998 | Gallant et al. | |
| 6,252,512 B1 | 6/2001 | Riley | |
| 6,344,794 B1 | 2/2002 | Ulrich et al. | |
| 7,868,740 B2 | 1/2011 | Mcneely et al. | |
| 9,165,449 B2 | 10/2015 | Ribble et al. | |
| 9,311,804 B2 * | 4/2016 | Ribble | A61B 5/1128 |
| 9,402,771 B2 * | 8/2016 | Carney | G08B 21/182 |
| 9,411,934 B2 | 8/2016 | Robinson et al. | |
| 9,545,342 B2 * | 1/2017 | Cretu-Petra | A61B 5/6802 |

(Continued)

OTHER PUBLICATIONS

PLOS, "Machine learning methods for detecting urinary tract infection and analysing daily living activities in people with dementia", link: https://journals.plos.org/plosone/article?id=10.1371/journal.pone.0209909, Retrieved on Jun. 2, 2020, pp. 1-13.

*Primary Examiner* — Shirley X Jian
(74) *Attorney, Agent, or Firm* — Barnes & Thornburg LLP

(57) ABSTRACT

An incontinence detection alert system may include a bed configured to receive an occupant and at least one monitor configured to acquire data related to at least one of a status of the bed or a status of the occupant. An incontinence detection system may have circuitry to detect an incontinence event of the occupant. A controller may be configured to receive the data from the at least one monitor and to further receive data related to a time of the incontinence event. A remote device may be configured to receive an alert from the controller before a predicted time of a future incontinence event.

21 Claims, 12 Drawing Sheets

(56) References Cited

U.S. PATENT DOCUMENTS

| | | | |
|---|---|---|---|
| 9,763,576 B2* | 9/2017 | Ribble | A61B 5/742 |
| 9,931,252 B2 | 4/2018 | Carney et al. | |
| 9,934,427 B2* | 4/2018 | Derenne | G08B 21/0476 |
| 10,115,291 B2* | 10/2018 | Tallent | A61F 13/42 |
| 10,159,607 B2* | 12/2018 | Monson | G06K 7/10356 |
| 10,172,522 B2* | 1/2019 | Ribble | A61B 5/01 |
| 10,311,694 B2 | 6/2019 | Mcintosh et al. | |
| 10,350,116 B2* | 7/2019 | Monson | A61B 5/7465 |
| 10,500,105 B2* | 12/2019 | Monson | A61F 13/42 |
| 10,517,784 B2* | 12/2019 | Zerhusen | A61G 7/0536 |
| 10,548,476 B2* | 2/2020 | Lane | A61B 5/6891 |
| 10,646,171 B2 | 5/2020 | Brasch et al. | |
| 10,685,249 B2* | 6/2020 | Zyglowicz | G06F 18/00 |
| 10,716,715 B2* | 7/2020 | Severns | G06K 7/10158 |
| 11,020,055 B1* | 6/2021 | Li | A61B 5/14507 |
| 11,020,284 B2* | 6/2021 | Severns | G06K 19/0709 |
| 11,096,837 B2* | 8/2021 | LaVon | A61F 13/514 |
| 11,135,110 B2* | 10/2021 | Zerhusen | A61G 7/05769 |
| 11,147,719 B2* | 10/2021 | Monson | A61B 5/6802 |
| 11,430,245 B2* | 8/2022 | Zyglowicz | A61B 5/20 |
| 11,478,383 B2* | 10/2022 | Severns | A61F 13/42 |
| 11,633,310 B2* | 4/2023 | LaVon | A61F 13/51401 |
| | | | 604/361 |
| 2008/0052030 A1* | 2/2008 | Olson | A61F 13/42 |
| | | | 702/189 |
| 2009/0056027 A1 | 3/2009 | Ball et al. | |
| 2013/0091631 A1 | 4/2013 | Hayes et al. | |
| 2013/0267791 A1* | 10/2013 | Halperin | A61B 5/742 |
| | | | 600/300 |
| 2014/0080413 A1 | 3/2014 | Hayes et al. | |
| 2014/0266736 A1* | 9/2014 | Cretu-Petra | A61B 5/6808 |
| | | | 340/573.5 |
| 2014/0327546 A1* | 11/2014 | Carney | A61F 13/42 |
| | | | 340/573.5 |
| 2015/0082542 A1 | 3/2015 | Hayes et al. | |
| 2015/0206151 A1* | 7/2015 | Carney | A61B 5/0002 |
| | | | 705/304 |
| 2015/0290060 A9 | 10/2015 | Hayes et al. | |
| 2015/0294549 A1* | 10/2015 | Ribble | A61G 7/0524 |
| | | | 340/573.5 |
| 2017/0293846 A1* | 10/2017 | Zyglowicz | G16H 10/65 |
| 2018/0221216 A1* | 8/2018 | Benz | A61F 13/53717 |
| 2018/0333306 A1* | 11/2018 | Ahong | A61F 13/42 |
| 2019/0254582 A1* | 8/2019 | Wei | G16H 40/67 |
| 2019/0320987 A1 | 10/2019 | Halperin et al. | |
| 2019/0336065 A1 | 11/2019 | Ricciardi et al. | |
| 2021/0205151 A1* | 7/2021 | Monson | A61F 13/42 |
| 2021/0401380 A1* | 12/2021 | Meyerson | A61G 7/0514 |

\* cited by examiner

INCONTINENCE PREDICTION SYSTEMS AND METHODS

CROSS-REFERENCE TO RELATED APPLICATIONS

This application claims priority under 35 U.S.C. § 119(e) to U.S. Provisional Application No. 63/043,819, filed Jun. 25, 2020, which is expressly incorporated by reference herein.

BACKGROUND

The present disclosure relates to an occupant support apparatus, and more particularly, to an occupant support apparatus having an incontinence prediction system and method.

Incontinence commonly occurs in acute and non-acute settings. When incontinence is unattended the consequences can be undesirable, such as leading to a urinary tract infection, which may progress to a more severe infection. Such infections can potentially lead to sepsis or skin breakdown, which may progress to bed sores and further infection. Several prior art products aim to reduce the response time to an incontinence event after it occurs, but these products do not eliminate the incontinence event prior to occurrence.

SUMMARY

The present disclosure includes one or more of the features recited in the appended claims and/or the following features which, alone or in any combination, may comprise patentable subject matter.

According to a first aspect of the disclosed embodiments, an incontinence detection alert system may include a bed configured to receive an occupant and at least one monitor configured to acquire data related to at least one of a status of the bed or a status of the occupant. An incontinence detection system may include circuitry to detect an incontinence event of the occupant. A controller may be configured to receive the data from the at least one monitor. The controller may be configured to further receive data related to a time of the incontinence event. The controller may be configured to compare the data from the at least one monitor and the data related to the time of the incontinence event to determine a correlation between the data from the at least one monitor and the data related to the time of the incontinence event. The controller may determine a predicted time of a future incontinence event based on the correlation between the data from the at least one monitor and the data related to the time of the incontinence event. A remote device may be configured to receive an alert from the controller before the predicted time of the future incontinence event.

In some embodiments of the first aspect, the controller may include a transceiver to transmit outgoing signals to the remote device and to receive incoming signals from the remote device. The remote device may be a remote computer. The remote device may be a mobile device of a caregiver. The remote device may receive the alert from the controller at least five minutes before the predicted time.

Optionally in the first aspect, the at least one monitor may include a movement detection system that determines when the occupant has exited the bed. The controller may correlate a time that the occupant exits the bed and the time of the incontinence event to determine a plurality of times that the occupant has required toileting. The plurality of times that the occupant has required toileting may be correlated to the predicted time of the future incontinence event.

It may be contemplated, in the first aspect, that the at least one monitor includes a memory that stores a time that the occupant receives at least one of food and fluids. A cart sensor may be configured to detect when a food cart is positioned under the bed. The controller may include at least one input. The time that the occupant receives at least one of food and fluids may be stored into the memory using the at least one input of the controller. The remote device may include at least one input. The time that the occupant receives at least one of food and fluids may be stored into the memory using the at least one input of the remote device. The controller may compare the time that the occupant receives at least one of food and fluids to the time of the incontinence event to determine a time lapse between the time that the occupant receives at least one of food and fluids and the time of the incontinence event. The predicted time of the future incontinence event may be determined based on the time lapse between the time that the occupant receives at least one of food and fluids and the time of the incontinence event.

It may be desired, in the first aspect, that the at least one monitor includes an angle sensor that determines a rotational angle of a mattress on the bed. The controller may determine a rotational angle of the mattress at the time of the incontinence event to determine a correlation between an occupant position and the time of the incontinence event. The controller may determine the predicted time of the future incontinence event based on the correlation between the occupant position and the time of the incontinence event.

In some embodiments of the first aspect, the at least one monitor may include an angle sensor that determines an angle of a head section of the bed. The controller may determine the angle of the head section at the time of the incontinence event to determine a correlation between an occupant position and the time of the incontinence event. The controller may determine the predicted time of the future incontinence event based on the correlation between the occupant position and the time of the incontinence event.

Optionally, in the first aspect, the at least one monitor may include a vital sign monitor. The controller may compare data from the vital sign monitor to the time of the incontinence event to determine a correlation between a vital sign of the occupant and the time of the incontinence event. The controller may determine the predicted time of the future incontinence event based on the correlation between the vital sign of the occupant and the time of the incontinence event.

According to a second aspect of the disclosed embodiments, a method of alerting a caregiver of future occupant incontinence may include acquiring data related to at least one of a status of a bed or a status of an occupant on the bed with at least one monitor. The method may also include detecting an incontinence event of the occupant with an incontinence detection system having circuitry to detect the incontinence event. The method may also include transmitting the data from the at least one monitor to a controller. The method may also include transmitting data related to a time of the incontinence event to the controller. The method may also include comparing the data from the at least one monitor and the data related to the time of the incontinence event to determine a correlation between the data from the at least one monitor and the data related to the time of the incontinence event. The method may also include determining a predicted time of a future incontinence event based on the correlation between the data from the at least one monitor and the data related to the time of the incontinence event. The method may also include sending an alert from the controller to a remote device before the predicted time of the future incontinence event.

In some embodiments of the second aspect, the method may also include transmitting outgoing signals to the remote device and to receiving incoming signals from the remote device with a transceiver of the controller. The remote device may be a remote computer. The remote device may be a mobile device of a caregiver. The method may also include sending the alert from the controller to the remote device at least five minutes before the predicted time.

Optionally, in the second embodiment, the method may also include determining when the occupant has exited the bed with a movement detection system. The method may also include correlating a time that the occupant exits the bed and the time of the incontinence event to determine a plurality of times that the occupant has required toileting. The method may also include correlating the plurality of times that the occupant has required toileting to the predicted time of the future incontinence event.

It may be contemplated, in the second embodiment, that the method may also include storing a time that the occupant receives at least one of food and fluids in a memory of the controller. The method may also include detecting when a food cart is positioned under the bed with a cart sensor. The method may also include inputting the time that the occupant receives at least one of food and fluids into the memory using at least one input of the controller. The method may also include inputting the time that the occupant receives at least one of food and fluids into the memory using at least one input of the remote device. The method may also include comparing the time that the occupant receives at least one of food and fluids to the time of the incontinence event to determine a time lapse between the time that the occupant receives at least one of food and fluids and the time of the incontinence event. The method may also include determining the predicted time of the future incontinence event based on the time lapse between the time that the occupant receives at least one of food and fluids and the time of the incontinence event.

It may be desired, in the second aspect, that the method may also include determining a rotational angle of a mattress on the bed with an angle sensor. The method may also include determining a rotational angle of the mattress at the time of the incontinence event to determine a correlation between an occupant position and the time of the incontinence event. The method may also include determining the predicted time of the future incontinence event based on the correlation between the occupant position and the time of the incontinence event.

In some embodiments of the second aspect, the method may also include determining an angle of a head section of the bed with an angle sensor. The method may also include determining the angle of the head section at the time of the incontinence event to determine a correlation between an occupant position and the time of the incontinence event. The method may also include determining the predicted time of the future incontinence event based on the correlation between the occupant position and the time of the incontinence event.

Optionally, in the second aspect, the method may also include monitoring a vital sign of an occupant with a vital sign monitor. The method may also include comparing data from the vital sign monitor to the time of the incontinence event to determine a correlation between the vital sign of the occupant and the time of the incontinence event. The method may also include determining the predicted time of the future incontinence event based on the correlation between the vital sign of the occupant and the time of the incontinence event.

According to a third aspect of the disclosed embodiments, an incontinence detection alert system may include a bed configured to receive an occupant and a movement detection system that determines when the occupant has exited the bed. An incontinence detection system may have circuitry to detect an incontinence event of the occupant. A controller may be configured to receive the data from the movement detection system. The controller may be configured to further receive data related to a time of the incontinence event. The controller may be configured to correlate a time that the occupant exits the bed and the time of the incontinence event to determine a plurality of times that the occupant has required toileting. The controller may determine a predicted time of a future incontinence event based on the plurality of times that the occupant has required toileting. A remote device may be configured to receive an alert from the controller before the predicted time of the future incontinence event.

In some embodiments of the third aspect, the controller may include a transceiver to transmit outgoing signals to the remote device and to receive incoming signals from the remote device. The remote device may be a remote computer. The remote device may be a mobile device of a caregiver. The remote device may receive the alert from the controller at least five minutes before the predicted time.

Optionally, in the third aspect, a memory may store a time that the occupant receives at least one of food and fluids. A cart sensor may be configured to detect when a food cart is positioned under the bed. The controller may include at least one input. The time that the occupant receives at least one of food and fluids may be stored into the memory using the at least one input of the controller. The remote device may include at least one input. The time that the occupant receives at least one of food and fluids may be stored into the memory using the at least one input of the remote device. The controller may compare the time that the occupant receives at least one of food and fluids to the time of the incontinence event to determine a time lapse between the time that the occupant receives at least one of food and fluids and the time of the incontinence event. The predicted time of the future incontinence event may be determined based on the time lapse between the time that the occupant receives at least one of food and fluids and the time of the incontinence event.

It may be desired, in the third aspect, that an angle sensor determines a rotational angle of a mattress on the bed. The controller may determine a rotational angle of the mattress at the time of the incontinence event to determine a correlation between an occupant position and the time of the incontinence event. The controller may determine the predicted time of the future incontinence event based on the correlation between the occupant position and the time of the incontinence event.

It may be contemplated, in the third aspect, that an angle sensor determines an angle of a head section of the bed. The controller may determine the angle of the head section at the time of the incontinence event to determine a correlation between an occupant position and the time of the incontinence event. The controller may determine the predicted time of the future incontinence event based on the correlation between the occupant position and the time of the incontinence event.

In some embodiments of the third aspect, a vital sign monitor may track a vital sign of the occupant. The controller may compare data from the vital sign monitor to the time of the incontinence event to determine a correlation between the vital sign of the occupant and the time of the incontinence event. The controller may determine the predicted time of the future incontinence event based on the correlation between the vital sign of the occupant and the time of the incontinence event.

According to a fourth aspect of the disclosed embodiments, an incontinence detection alert system may include a bed configured to receive an occupant and a memory that stores a time that the occupant receives at least one of food and fluids. An incontinence detection system may have circuitry to detect an incontinence event of the occupant. A controller may be configured to receive the data from the memory. The controller may be configured to further receive data related to a time of the incontinence event. The controller may be configured to compare the time that the occupant receives at least one of food and fluids to the time of the incontinence event to determine a time lapse between the time that the occupant receives at least one of food and fluids and the time of the incontinence event. The controller may determine a predicted time of a future incontinence event based on the time lapse between the time that the occupant receives at least one of food and fluids and the time of the incontinence event. A remote device may be configured to receive an alert from the controller before the predicted time of the future incontinence event.

In some embodiments of the fourth aspect, the controller may include a transceiver to transmit outgoing signals to the remote device and to receive incoming signals from the remote device. The remote device may be a remote computer. The remote device may be a mobile device of a caregiver. The remote device may receive the alert from the controller at least five minutes before the predicted time. A cart sensor may be configured to detect when a food cart is positioned under the bed. The controller may include at least one input. The time that the occupant receives at least one of food and fluids may be stored into the memory using the at least one input of the controller. The remote device may include at least one input. The time that the occupant receives at least one of food and fluids may be stored into the memory using the at least one input of the remote device.

Optionally, in the fourth aspect, an angle sensor may determine a rotational angle of a mattress on the bed. The controller may determine a rotational angle of the mattress at the time of the incontinence event to determine a correlation between an occupant position and the time of the incontinence event. The controller may determine the predicted time of the future incontinence event based on the correlation between the occupant position and the time of the incontinence event.

It may be desired, in the fourth aspect, that an angle sensor determines an angle of a head section of the bed. The controller may determine the angle of the head section at the time of the incontinence event to determine a correlation between an occupant position and the time of the incontinence event. The controller may determine the predicted time of the future incontinence event based on the correlation between the occupant position and the time of the incontinence event.

It may be contemplated, in the fourth aspect, that a vital sign monitor tracks a vital sign of an occupant. The controller may compare data from the vital sign monitor to the time of the incontinence event to determine a correlation between the vital sign of the occupant and the time of the incontinence event. The controller may determine the predicted time of the future incontinence event based on the correlation between the vital sign of the occupant and the time of the incontinence event.

In some embodiments of the fourth aspect, a movement detection system determines when the occupant has exited the bed. The controller may correlate a time that the occupant exits the bed and the time of the incontinence event to determine a plurality of times that the occupant has required toileting. The plurality of times that the occupant has required toileting may be correlated to the predicted time of the future incontinence event.

According to a fifth aspect of the disclosed embodiments, an incontinence detection alert system may include a bed configured to receive an occupant and a rotational angle sensor that determines a rotational angle of a mattress on the bed. An incontinence detection system may have circuitry to detect an incontinence event of the occupant. A controller may be configured to receive the data from the rotational angle sensor. The controller may be configured to further receive data related to a time of the incontinence event. The controller may be configured to determine a rotational angle of the mattress at the time of the incontinence event to determine a correlation between an occupant position and the time of the incontinence event. The controller may determine a predicted time of a future incontinence event based on the correlation between the occupant position and the time of the incontinence event. A remote device may be configured to receive an alert from the controller before the predicted time of the future incontinence event.

In some embodiments of the fifth aspect, the controller may include a transceiver to transmit outgoing signals to the remote device and to receive incoming signals from the remote device. The remote device may be a remote computer. The remote device may be a mobile device of a caregiver. The remote device may receive the alert from the controller at least five minutes before the predicted time.

Optionally, in the fifth aspect, a movement detection system may determine when the occupant has exited the bed. The controller may correlate a time that the occupant exits the bed and the time of the incontinence event to determine a plurality of times that the occupant has required toileting. The plurality of times that the occupant has required toileting may be correlated to the predicted time of the future incontinence event.

It may be desired, in the fifth aspect, that a memory stores a time that the occupant receives at least one of food and fluids. A cart sensor may be configured to detect when a food cart is positioned under the bed. The controller may include at least one input. The time that the occupant receives at least one of food and fluids may be stored into the memory using the at least one input of the controller. The remote device may include at least one input. The time that the occupant receives at least one of food and fluids may be stored into the memory using the at least one input of the remote device. The controller may compare the time that the occupant receives at least one of food and fluids to the time of the incontinence event to determine a time lapse between the time that the occupant receives at least one of food and fluids and the time of the incontinence event. The predicted time of the future incontinence event may be determined based on the time lapse between the time that the occupant receives at least one of food and fluids and the time of the incontinence event.

It may be contemplated, in the fifth aspect, that a head angle sensor determines an angle of a head section of the bed. The controller may determine the angle of the head section at the time of the incontinence event to determine a correlation between an occupant position and the time of the incontinence event. The controller may determine the predicted time of the future incontinence event based on the correlation between the occupant position and the time of the incontinence event.

In some embodiments of the fifth aspect, a vital sign monitor may track a vital sign of the occupant. The controller may compare data from the vital sign monitor to the time of the incontinence event to determine a correlation between the vital sign of the occupant and the time of the incontinence event. The controller may determine the predicted time of the future incontinence event based on the correlation between the vital sign of the occupant and the time of the incontinence event.

According to a sixth aspect of the disclosed embodiments, an incontinence detection alert system may include a bed configured to receive an occupant and a head angle sensor that determines an angle of a head section of the bed. An incontinence detection system may have circuitry to detect an incontinence event of the occupant. A controller may be configured to receive the data from the head angle sensor. The controller may be configured to further receive data related to a time of the incontinence event. The controller may be configured to determine the angle of the head section at the time of the incontinence event to determine a correlation between an occupant position and the time of the incontinence event. The controller may determine a predicted time of a future incontinence event based on the correlation between the occupant position and the time of the incontinence event. A remote device may be configured to receive an alert from the controller before the predicted time of the future incontinence event.

In some embodiments of the sixth aspect, the controller may include a transceiver to transmit outgoing signals to the remote device and to receive incoming signals from the remote device. The remote device may be a remote computer. The remote device may be a mobile device of a caregiver. The remote device may receive the alert from the controller at least five minutes before the predicted time.

Optionally, in the sixth aspect, a movement detection system may determine when the occupant has exited the bed. The controller may correlate a time that the occupant exits the bed and the time of the incontinence event to determine a plurality of times that the occupant has required toileting. The plurality of times that the occupant has required toileting may be correlated to the predicted time of the future incontinence event.

It may be contemplated, in the sixth aspect, that a memory stores a time that the occupant receives at least one of food and fluids. A cart sensor may be configured to detect when a food cart is positioned under the bed. The controller may include at least one input. The time that the occupant receives at least one of food and fluids may be stored into the memory using the at least one input of the controller. The remote device may include at least one input. The time that the occupant receives at least one of food and fluids may be stored into the memory using the at least one input of the remote device. The controller may compare the time that the occupant receives at least one of food and fluids to the time of the incontinence event to determine a time lapse between the time that the occupant receives at least one of food and fluids and the time of the incontinence event. The predicted time of the future incontinence event may be determined based on the time lapse between the time that the occupant receives at least one of food and fluids and the time of the incontinence event.

It may be desired, in the sixth aspect, that a rotational angle sensor determines a rotational angle of a mattress on the bed. The controller may determine a rotational angle of the mattress at the time of the incontinence event to determine a correlation between an occupant position and the time of the incontinence event. The controller may determine the predicted time of the future incontinence event based on the correlation between the occupant position and the time of the incontinence event.

In some embodiments of the sixth aspect, a vital sign monitor may track a vital sign of the occupant. The controller may compare data from the vital sign monitor to the time of the incontinence event to determine a correlation between a vital sign of the occupant and the time of the incontinence event. The controller may determine the predicted time of the future incontinence event based on the correlation between the vital sign of the occupant and the time of the incontinence event.

According to a seventh aspect of the disclosed embodiments, an incontinence detection alert system may include a bed configured to receive an occupant and a vital sign monitor to track a vital sign of the occupant. An incontinence detection system may have circuitry to detect an incontinence event of the occupant. A controller may be configured to receive the data from the vital sign monitor, the controller configured to further receive data related to a time of the incontinence event. The controller may be configured to compare data from the vital sign monitor to the time of the incontinence event to determine a correlation between the vital sign of the occupant and the time of the incontinence event. The controller may determine a predicted time of a future incontinence event based on the correlation between the vital sign of the occupant and the time of the incontinence event. A remote device may be configured to receive an alert from the controller before the predicted time of the future incontinence event.

In some embodiments of the seventh aspect, the controller may include a transceiver to transmit outgoing signals to the remote device and to receive incoming signals from the remote device. The remote device may be a remote computer. The remote device may be a mobile device of a caregiver. The remote device may receive the alert from the controller at least five minutes before the predicted time.

Optionally, in the seventh aspect, a movement detection system may determine when the occupant has exited the bed. The controller may correlate a time that the occupant exits the bed and the time of the incontinence event to determine a plurality of times that the occupant has required toileting. The plurality of times that the occupant has required toileting may be correlated to the predicted time of the future incontinence event.

It may be contemplated, in the seventh aspect, that a memory stores a time that the occupant receives at least one of food and fluids. A cart sensor may be configured to detect when a food cart is positioned under the bed. The controller may include at least one input. The time that the occupant receives at least one of food and fluids may be stored into the memory using the at least one input of the controller. The remote device may include at least one input. The time that the occupant receives at least one of food and fluids may be stored into the memory using the at least one input of the remote device. The controller may compare the time that the occupant receives at least one of food and fluids to the time of the incontinence event to determine a time lapse between the time that the occupant receives at least one of food and fluids and the time of the incontinence event. The predicted time of the future incontinence event may be determined based on the time lapse between the time that the occupant receives at least one of food and fluids and the time of the incontinence event.

It may be desired, in the seventh aspect, that an angle sensor determines a rotational angle of a mattress on the bed. The controller may determine a rotational angle of the mattress at the time of the incontinence event to determine a correlation between an occupant position and the time of the incontinence event. The controller may determine the predicted time of the future incontinence event based on the correlation between the occupant position and the time of the incontinence event.

Optionally, in the seventh aspect, an angle sensor may determine an angle of a head section of the bed. The controller may determine the angle of the head section at the time of the incontinence event to determine a correlation between an occupant position and the time of the incontinence event. The controller may determine the predicted time of the future incontinence event based on the correlation between the occupant position and the time of the incontinence event.

According to an eight aspect of the disclosed embodiments, an incontinence detection alert system may include a bed configured to receive an occupant. At least one monitor may be configured to acquire data related to at least one of a status of the bed or a status of the occupant. An incontinence detection system may have circuitry to detect an incontinence event of the occupant. A controller may be configured to receive the data from the at least one monitor. The controller may further be configured to also receive data relating to the incontinence event detected by the incontinence detection system. The controller may determine a predicted upcoming future incontinence event based on the data from the at least one monitor and the data related to the incontinence event. A remote device may be configured to receive an alert from the controller regarding the predicted future incontinence event.

In some embodiments of the eighth aspect, the incontinence detection system may include an incontinence detection pad. The incontinence detection system may include a diaper. The remote device may display a predicted time that the incontinence event is predicted to occur. The remote device may display a time range that the incontinence event is predicted to occur. The remote device may display a time period in the future that the incontinence event is predicted to occur. The controller may include a transceiver to transmit outgoing signals to the remote device and to receive incoming signals from the remote device. The remote device may be a remote computer. The remote device may be a mobile device of a caregiver. The remote device may receive the alert from the controller at least five minutes before the predicted future incontinence event.

Optionally, in the eighth aspect, the at least one monitor may include a movement detection system that determines when the occupant has exited the bed. The at least one monitor may include a memory that stores a time that the occupant receives at least one of food and fluids. The at least one monitor may include an angle sensor that determines a rotational angle of a mattress on the bed. The at least one monitor may include an angle sensor that determines an angle of a head section of the bed. The at least one monitor may include a vital sign monitor.

In some embodiments of any of the above aspects, the incontinence detection system may include a diaper. The incontinence detection system may include an incontinence detection pad.

Additional features, which alone or in combination with any other feature(s), such as those listed above and/or those listed in the claims, can comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which.

DETAILED DESCRIPTION

Figure 1:
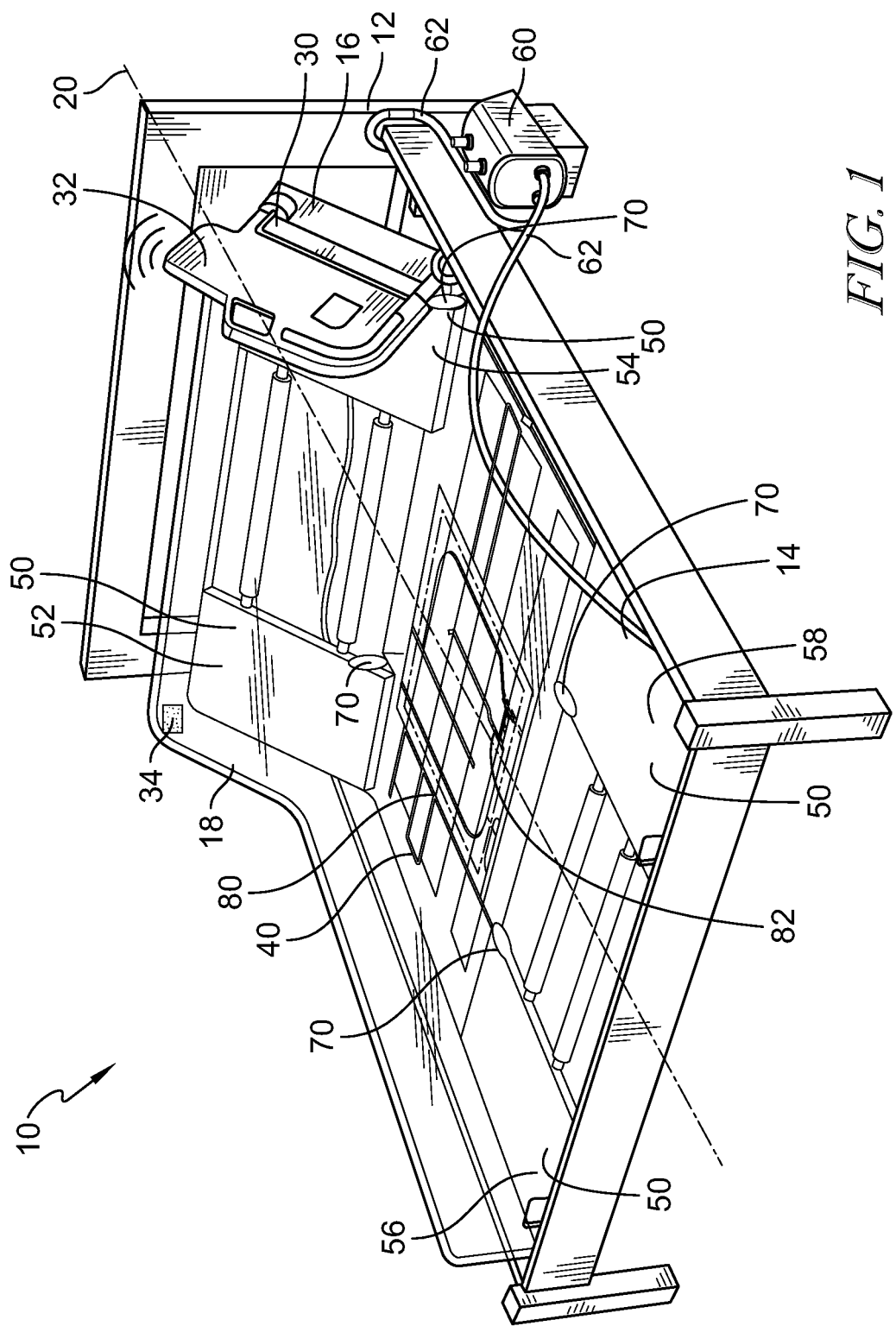
FIG. 1 is a side perspective view of a bed equipped with an incontinence detection system having circuitry to detect an incontinence event of an occupant of the bed and a plurality of monitors that collect data related to at least one of a status of the bed or a status of the occupant.

Referring to FIG. 1, an occupant support apparatus 10 embodied as a bed includes a frame 12 having a seat section or lower body section 14 and a head section or upper body section 16. A mattress 18 extends along the frame 12 from the seat section 14 to the head section 16. The apparatus 10 is configured as a bed for a home that has been modified with various monitors for tracking data related to a status of the bed or the status of an occupant in the bed. In other embodiments, as described below, the apparatus 10 may be a hospital bed in a healthcare facility that is configured for a patient. The head section 16 of the apparatus 10 is configured to rotate relative to the seat section 14 about a longitudinal axis 20 of the apparatus 10. The apparatus 10 is illustrated with the head section 16 raised relative to the seat section 14. The apparatus 10 also includes at least one siderail 30. In the illustrative embodiment, the siderail 30 is coupled to the head section 16. The present disclosure contemplates that the siderail 30 is coupled to the seat section 14, in some embodiments. A controller 32 is coupled to the siderail 30; however, in some embodiments, the controller 32 is coupled to other parts of the frame 12. The controller 32 is configured to receive data from the various monitors to predict a future incontinence event of the occupant.

A head angle sensor 34 is coupled to the head section 16 and configured to monitor an angle of the head section 16 relative to the seat section 14 about the longitudinal axis 20 of the apparatus 10. The head angle sensor 34 may include an accelerometer or other like devices such as an inclinometer, rotary potentiometer, one or more mercury switches, one or more ball switches or the like, to measure the angle of the head section 16. The head angle sensor 34 transmits data indicative of the angle to the controller 32. In some embodiments, the head angle sensor 34 includes, or is coupled to, a wireless transmitter or transceiver to send the data to the controller 32. In other embodiments, the head angle sensor 34 is wired to the controller 32.

A movement monitor 40 is positioned under the mattress 18. In the illustrative embodiment, the movement monitor 40 is positioned in or beneath the seat section 14; however, in some embodiments, the movement monitor 40 may be position in or beneath the head section 16. The movement monitor 40 includes at least one sensor, for example one or more load cells (e.g., strain gage based load cells), one or more force sensitive resistors (FSR's), one or more capacitive sensors, one or more piezoelectric sensors, or the like, that measures force or pressure at various locations of the mattress 18. The movement monitor 40 transmits signals to the controller 32 indicative of the measured forces or pressures, as the case may be. For example, the movement monitor 40 may include or be coupled to a transmitter or transceiver that wirelessly transmits the signals to the controller 32. In other embodiments, the movement monitor 40 is wired to the controller 32. The controller 32 monitors the signals from the movement monitor 40 to determine whether the occupant is exiting or has exited the apparatus 10. For example, increases in pressure on one side of the mattress 18 may indicate that the occupant is exiting the apparatus 10 on that side of the mattress 18. In another example, a complete loss of pressure or force on the mattress 18 may indicate that the occupant is no longer positioned on the apparatus 10.

The illustrative apparatus 10 also includes a plurality of bladders 50 positioned between the frame 12 and the mattress 18. In the illustrative embodiment, a right head bladder 52 and a left head bladder 54 are positioned in the head section 16. A right seat bladder 56 and a left seat bladder 58 are positioned in the seat section 14. The bladders 50 are selectively inflated and deflated by a blower 60 and accompanying valves to laterally rotate a section of the mattress 18 relative to the longitudinal axis 20. In the illustrative embodiment, the blower 60 is positioned next to the apparatus 10, uncoupled to the frame 12, and includes hoses 62 that couple the blower 60 to the bladders 50. In another embodiment, discussed in more detail below, the blower 60 may be integrated into the apparatus 10, for example, integrated in the frame 12 or the mattress 18. The right head bladder 52 and the right seat bladder 56 may be inflated to raise the right side of the mattress 18 to provide right side lateral rotation of the occupant which turns the occupant toward their left side. In another example, the left head bladder 54 and the left seat bladder 58 may be inflated to raise the left side of the mattress 18 to provide left side lateral rotation of the occupant which turns the occupant toward their right side.

A plurality of rotational angle sensors 70 are positioned on the mattress 18 in the illustrative example. Each sensor 70 is positioned adjacent one of the bladders 50. The rotational angle sensors 70 are configured to monitor a rotational angle of the mattress 18, e.g., a right lateral rotation angle or a left lateral rotation angle. The rotational angle sensors 70 send signals to the controller 32 indicative of the lateral rotation angle of the mattress 18. The rotational angle sensors 70 may include or be coupled to a transmitter or transceiver that wirelessly transmits the signals to the controller 32 or, in other embodiments, the rotational angle sensors 70 may be wired to the controller 32. Accordingly, the controller 32 may monitor the lateral rotation angle of the mattress 18.

An incontinence detection system 80 having circuitry 82 to detect incontinence is positioned on the mattress 18. In some embodiments, as shown, in FIG. 2, the incontinence detection system 80 is an incontinence pad 90 that is positioned on the mattress 18 under the occupant. In other embodiments, as shown FIG. 3, the incontinence detection system 80 is a diaper 100 that is worn by the occupant. This is not to exclude the possibility that the incontinence pad 90 and diaper 100 may be used simultaneously. The incontinence detection system 80 detects incontinence events of the occupant and sends signals to the controller 32 indicative of an incontinence event. For example, the incontinence detection system 80 may communicate via wireless communications with the controller 32, e.g., through a radio-frequency identification (RFID) tag. Accordingly, as described in more detail below, the controller 32 can track incontinence events and correlate a time of such events to other data monitored by the controller 32.

Figure 2:
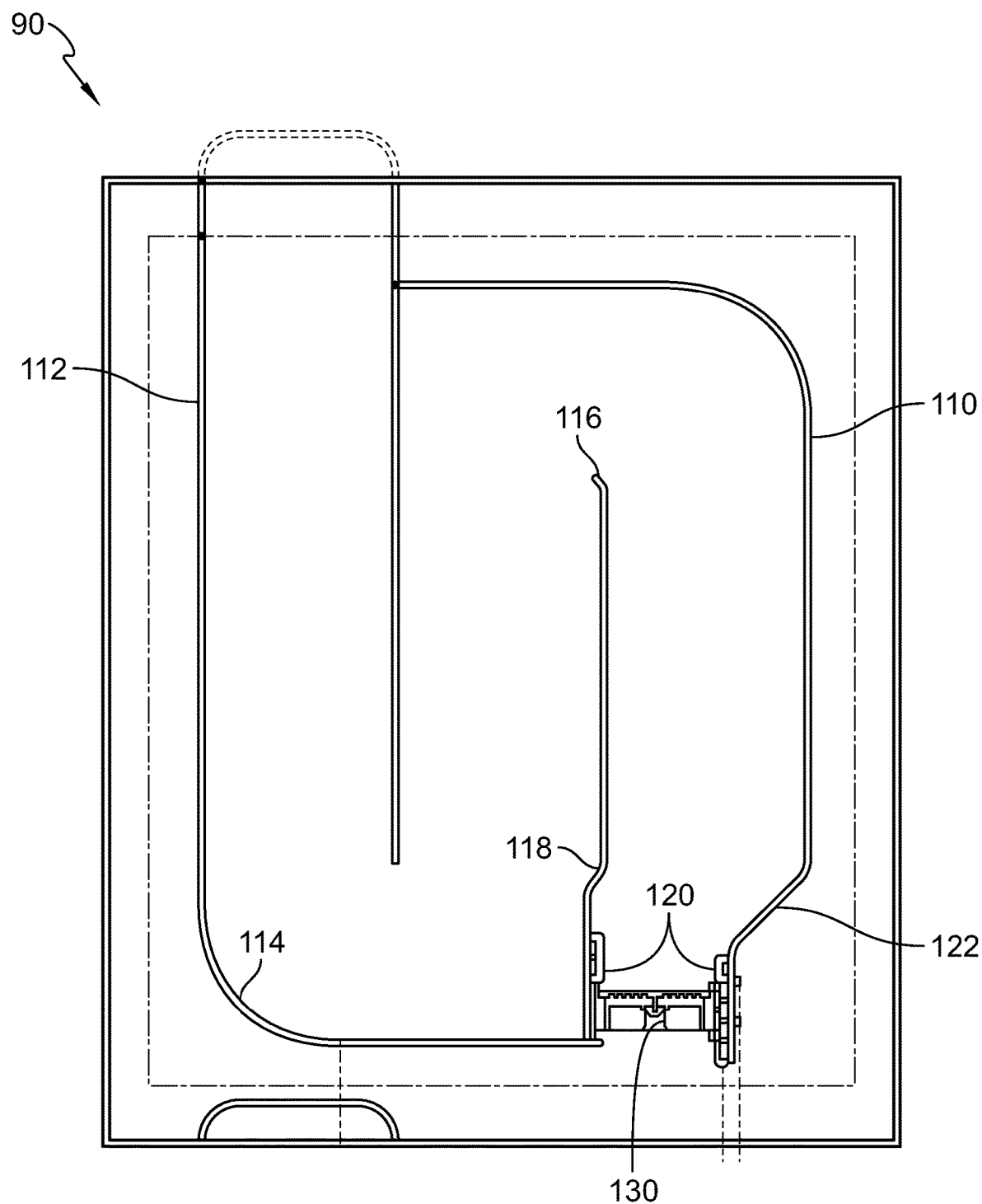
FIG. 2 is a schematic view of the incontinence detection system embodied as an incontinence detection pad.

Referring now to FIG. 2, the incontinence pad 90 includes first and second electrode traces 110, 112. The traces 110, 112 each include a quarter of a circle trace portion 114 having a radius of about 121.5 mm in the illustrative example. Trace portions 114 are located at diagonally opposite corner regions of the incontinence pad 90. The trace 112 also includes a hook portion 116 at a terminal end thereof. Segments of the electrode traces 110, 112 other than the portions 114, 116 are generally straight, although, electrode trace 110 has an inclined segment 118 leading to redundancy means 120 of the trace 110 and the electrode trace 112 has an inclined segment 122 spaced above redundancy means 120, with 118 being longer than 122.

A passive RFID tag 130 couples the first and second electrode traces 110, 112. When fluid is present between the first and second electrode traces 110, 112 a signal is sent to the RFID tag 130 indicative of an incontinence event. The RFID tag 130 relays this signal to the controller 32 so that the controller 32 can monitor and track detected incontinence events. Additional details of incontinence pad 90 can be found in U.S. Patent Application Publication No. 2019/0060137 A1 which is hereby incorporated by reference herein for all that it teaches to the extent not inconsistent with the present disclosure which shall control as to any inconsistencies.

Figure 3:
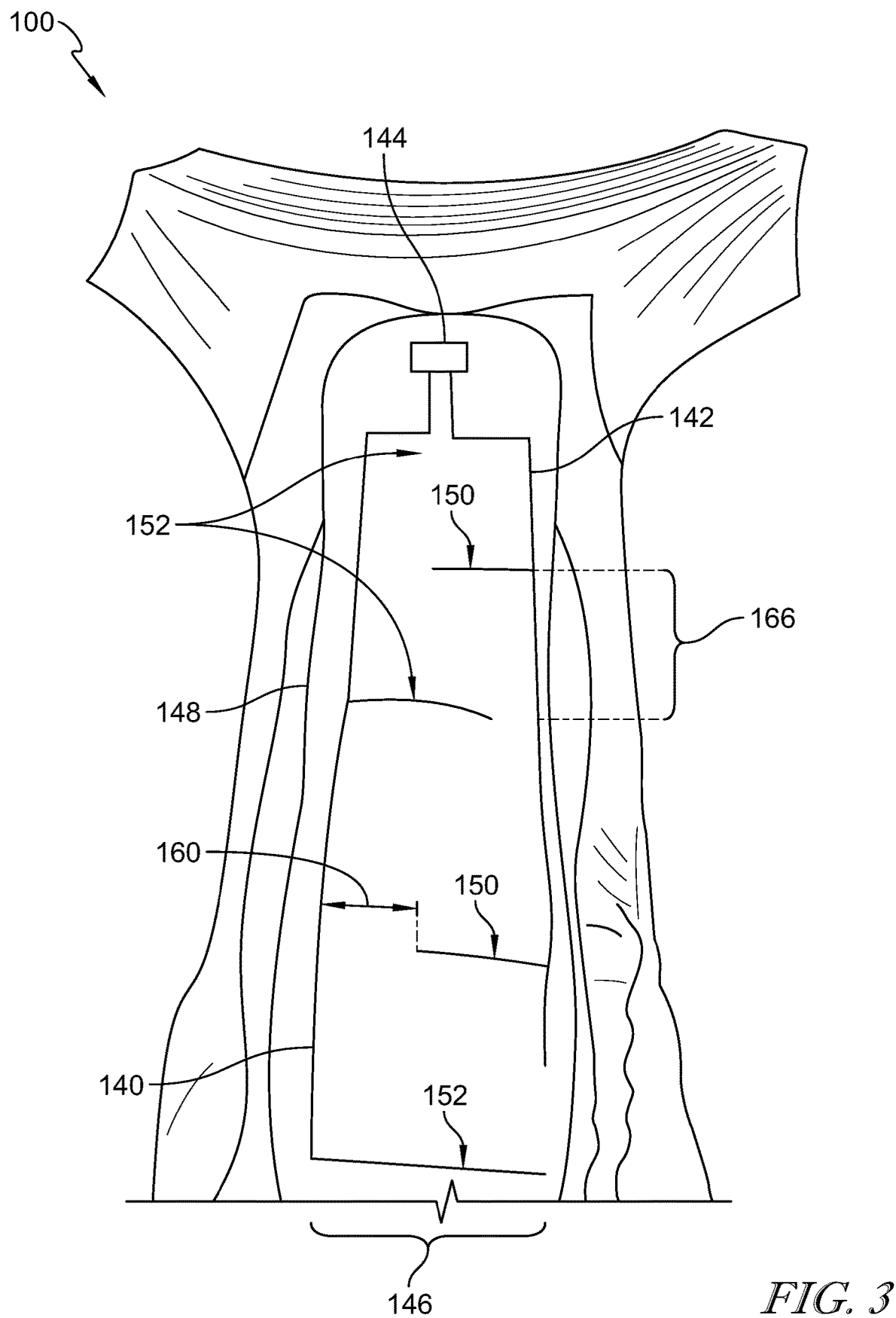
FIG. 3 is a schematic view of the incontinence detection system embodied as a diaper.

Referring now to FIG. 3, the diaper or other wearable pad 100 includes connector traces 140, 142 extending from a passive RFID tag 144 and extending longitudinally in substantially parallel relation along the outer edges of a moisture zone 146 of the diaper or wearable pad 100. In some embodiments, shielding material or a shield 148 coats or otherwise overlies each of the connector traces 140, 142 to prevent the connector traces from being exposed to moisture without the moisture first being absorbed in the absorbent material of the diaper 100. Alternatively or additionally, connector traces 140, 142 lie outside moisture zone 146 in some embodiments so as to inhibit any chance for exposure to moisture that is present within zone 146. In some embodiments therefore, shields 148 are not needed for covering traces 140.

First and second sets of sensor traces 150, 152 extend from respective connector traces 140, 142 in a direction substantially perpendicular to the traces 140, 142. The traces 150, 152 extend across the moisture zone 146 but terminate prior to reaching the opposite trace 140, 142. Thus, in the illustrative example, the traces 150 each extend from the trace 142 and terminal ends of the traces 150 are spaced from the trace 140. Similarly, the traces 152 each extend from the trace 140 and terminal ends of the traces 152 are spaced from the trace 142. A distance 160 (shown in FIG. 3 between the terminal end of one of the traces 150 and the trace 140) is provided between each terminal end of the traces 150, 152 and the trace 140, 142 spaced therefrom.

The first 150 and second traces 152 are arranged in an alternating pattern along the length of the diaper 100. Thus, the trace 142 and its accompany traces 152 form a first comb-like pattern and the trace 140 and its accompanying traces 150 form a second comb-like pattern. The comb-like patterns are arranged so that the traces 150 are interdigitated with the traces 152. The spacing distance 160 is smaller than a spacing 166 between adjacent traces 150, 152. Because of the shielding 148 covering the traces 140, 142, moisture that would otherwise make an electrical connection between terminal ends of the traces 150, 152 and the traces 140, 142 spaced therefrom by distance 160, is unable to do so. Instead, an electrical connection is made between traces 140, 142 only when sufficient moisture is present to expose a first and second sensor trace 150, 152 to moisture across the distance 166. For example, in some embodiments contemplated herein, the distance 166 between the first and second sensor traces 150, 152 requires that 150 milliliters (ml) of moisture or liquid be present within the moisture zone 146 before an electrical connection is made between adjacent traces 150, 152. Thus, the distance 166 is selected in the illustrative example so that a signal from the RFID tag 144 is generated in response to moisture contacting one first sensing trace 150 and one second sensing trace 152 which occurs when about 150 milliliters (ml) of moisture is present in the moisture zone 146.

By shielding the connecting traces 140, 142 with moisture resistant layers (not shown) that comprise shields 148, oversensitivity may be avoided such that a signal may only be generated when a prescribed fluid volume is present in the moisture zone 146. This prevents, for example, incontinence signals being sent by the RFID tag 144 in response to perspiration or other moisture that bridges across any of the spaces 160. Alternatively, the connecting traces 140, 142 are positioned outside of the moisture zone 146 as mentioned above to achieve a similar result. The first sensing traces 150 and second sensing traces 152 are spaced apart by a predetermined distance 166 that is based on a desired moisture sensitivity which also takes into account the wicking and absorbency properties of the diaper or other wearable pad 100 within the zone 146. According to the present disclosure, shielded connector traces, similar to the traces 140, 142, and unshielded sensor traces, similar to the traces 150, 152, also may be used in non-wearable pad embodiments, such each of the other pad embodiments disclosed herein.

Figure 4:
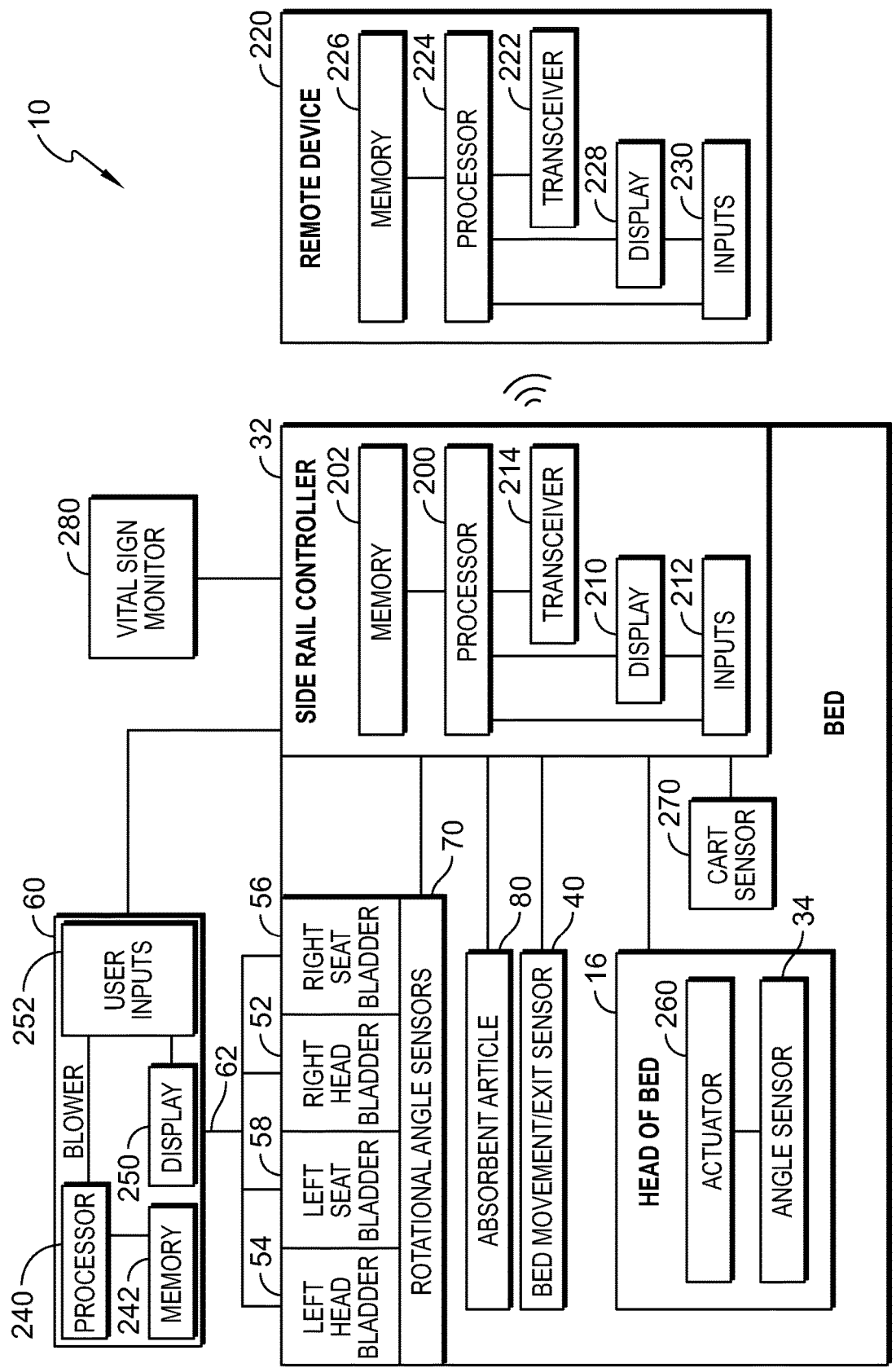
FIG. 4 is a schematic view of the bed shown in FIG. 1 having the incontinence detection system and the plurality of monitors.

Referring now to FIG. 4, the controller 32 is positioned on the siderail 30 of the apparatus 10. The controller 32 includes one or more microprocessors 200 or microcontrollers that execute software to perform the various control functions and algorithms described herein. Thus, the controller 32 also includes a memory device 202 for storing software, variables, calculated values, and the like as is well known in the art. The processor 200 is configured to execute instructions stored in the memory device 202 to perform the routines described in more detail below. The controller 32 also includes a display 210 for displaying information to a user, for example, a caregiver, and at least one user input 212 for inputting commands into the controller 32. A transceiver 214 is included in the controller 32 to communicate with a remote device 220. In the exemplary embodiment, the remote device 220 is a mobile device, such as a mobile phone or tablet computer, of a caregiver. In other embodiments, the remote device 220 may be a remote computer, e.g., a computer at a nurse's station. The remote device 220 also includes a transceiver 222 for communicating with the controller 32. For example, the controller 32 may send signals to or receive signals from the remote device 220.

The remote device 220 includes one or more microprocessors 224 or microcontrollers that execute software to perform the various control functions and algorithms described herein. Thus, the remote device 220 also includes a memory device 226 for storing software, variables, calculated values, and the like as is well known in the art. The processor 224 is configured to execute instructions stored in the memory device 226 to perform the routines described in more detail below. The remote device 220 also includes a display 228 for displaying information to a user, for example, a caregiver, and at least one user input 230 for inputting commands into the remote device 220.

The right head bladder 52 and the left head bladder 54 are positioned in the head section 16. The right seat bladder 56 and the left seat bladder 58 are positioned in the seat section 14. The rotational angle sensors 70 are positioned adjacent the bladders 50 and are configured to detect a lateral rotation angle of the mattress 18. The rotational angle sensors 70 are in communication with the controller 32. The blower 60 is coupled to the bladders 50 via the hoses 62. In the illustrated embodiment, the blower 60 is positioned outside of the apparatus 10, for example, on the floor next to the apparatus 10. The blower 60 includes one or more microprocessors 240 or microcontrollers that execute software to perform the various control functions and algorithms described herein. Thus, the blower 60 also includes a memory device 242 for storing software, variables, calculated values, and the like as is well known in the art. The processor 240 is configured to execute instructions stored in the memory device 242 to inflate and deflate the bladders 50 as described herein. For example, a caregiver may enter a command with the user inputs 230 of the controller to laterally rotate the occupant. The controller 32 may then send a signal to the blower 60 to inflate or deflate at least one of the bladders 50. In another embodiment, the blower 60 includes a display 250 and user inputs 252 to enter the commands to laterally rotate the mattress 18.

The head section 16 of the apparatus 10 includes an actuator 260, for example a pneumatic actuator 260 that raises and lowers the head section 16 relative to the seat section 14. In some embodiments, the head section 16 does not include an actuator 260 and the head section 16 is manually raised and lowered by a caregiver. In some embodiments, the actuator 260 may a linear actuator for automated mechanical actuation. The head angle sensor 34 detects the angle of the head section 16 and sends signals to the controller 32 indicative of the angle of the head section 16.

The incontinence detection system 80 is positioned either on the mattress 18, e.g., as an incontinence detection pad 90, or on the occupant, e.g., as a diaper 100. The incontinence detection system 80 communicates with the controller 32 and sends signals to the controller 32 indicative of an incontinence event. Likewise, the movement monitor 40 detects when the occupant has exited the apparatus 10. The movement monitor 40 sends signals to the controller 32 indicative of bed exit detection.

A cart sensor 270 is provided to detect when a food cart (not shown) has its base positioned under the apparatus 10. For example, most food carts are made from metal. In such an embodiment, the sensor 270 may include an inductor or capacitor that detects the presence of metal under the apparatus 10. In another embodiment, the sensor 270 may include an RFID tag reader that reads a corresponding RFID tag on the food cart. The sensor 270 is configured to transmit signals to the controller 32 indicative of the presence of the food cart.

A vital signs monitor 280 may also be positioned near the apparatus 10 and coupled to the occupant. The vital signs monitor 280 monitors vital signs of the occupant, e.g. heartrate, blood pressure, respiratory rate, or the like. In some embodiments, the vital signs monitor 280 may be at least one of a heart rate monitor, a respiration rate monitor, a blood pressure monitor, a temperature monitor, or a pulse oximeter. The vital signs monitor 280 communicates with the controller 32 to send signals to the controller 32 indicative of a vital sign of the occupant.

Figure 5:
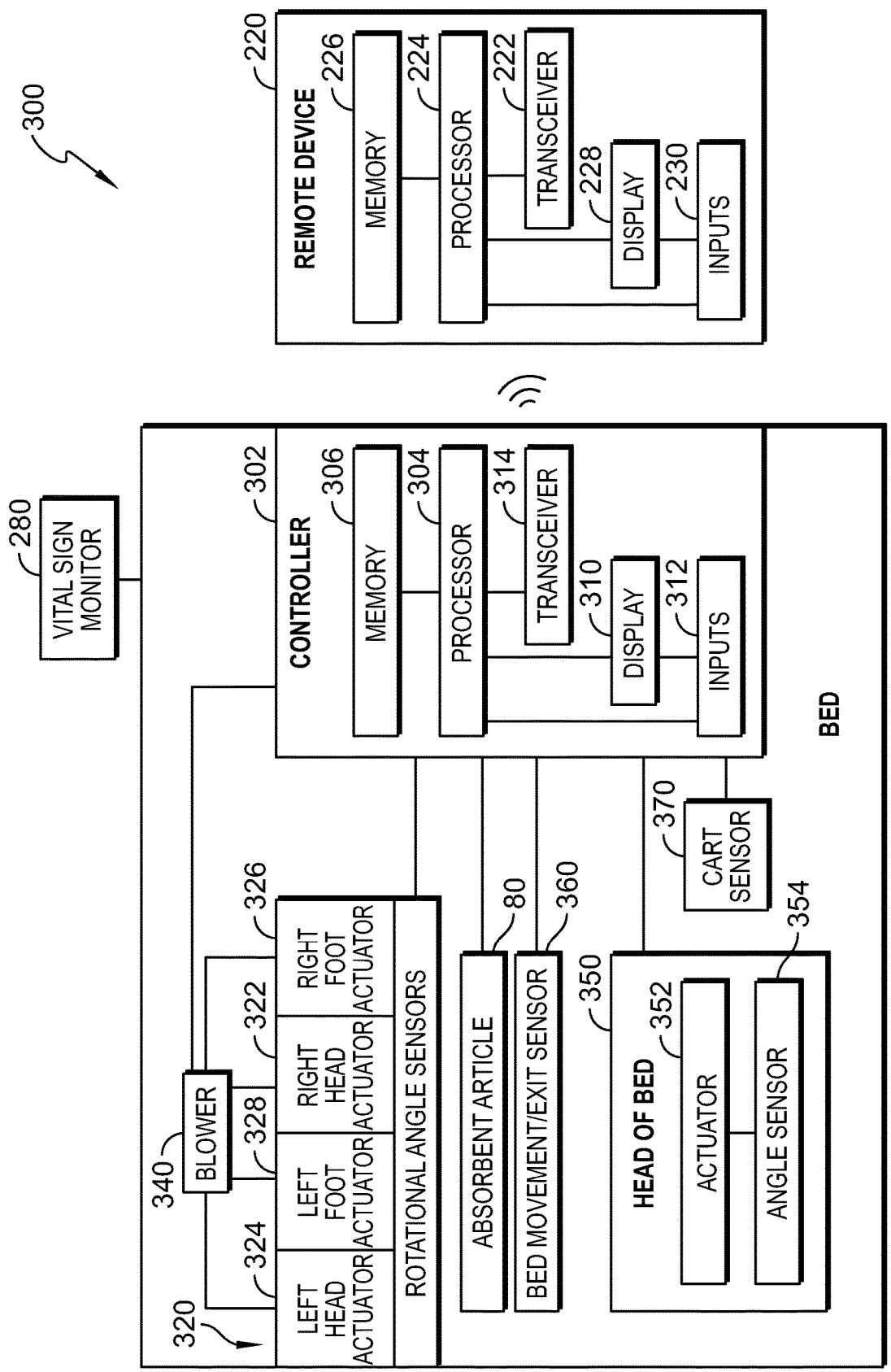
FIG. 5 is a schematic view of another embodiment of a bed having the incontinence detection system and the plurality of monitors.

Referring to FIG. 5, a hospital bed 300 includes a controller 302 that is incorporated into the bed 300, for example, into a siderail, head board, or foot board of the bed 300. The controller 302 includes one or more microprocessors 304 or microcontrollers that execute software to perform the various control functions and algorithms described herein. Thus, the controller 302 also includes a memory device 306 for storing software, variables, calculated values, and the like as is well known in the art. The processor 304 is configured to execute instructions stored in the memory device 306 to perform the routines described in more detail below. The controller 302 also includes a display 310 for displaying information to a user, for example, a caregiver, and at least one user input 312 for inputting commands into the controller 302. A transceiver 314 is included in the controller 302 to communicate with the remote device 220. The remote device 220 is described in detail above.

A plurality of actuators 320 includes a right head actuator 322, left head actuator 324, a right seat actuator 326, and a left seat actuator 328. The actuators 320 may be linear actuators for automated mechanical actuation. Rotational angle sensors 330 are positioned adjacent the bladders 320 and are configured to detect a lateral rotation angle of a mattress. The rotational angle sensors 330 are in communication with the controller 302. In some embodiments, the actuators 320 may be inflatable bladders that are inflated and deflated using the blower 340. The blower 340 is positioned in the bed 300 and coupled to the bladders 320 such as through one or more valves, manifolds, and/or conduits. The processor 304 is configured to execute instructions stored in the memory device 306 to raise and lower the actuators 320. For example, a caregiver may enter a command with the user inputs 312 to laterally rotate the occupant. In one embodiment, the controller 302 may then send a signal to the blower 340 to inflate or deflate at least one of the actuators 320. In another embodiment, the controller 302 may then send a signal to the linear actuator to raise and lower a respective section of the bed 300.

A head section 350 of the bed 300 includes an actuator 352, for example a pneumatic actuator that raises and lowers the head section 350. A head angle sensor 354 detects the angle of the head section 350 and sends signals to the controller 302 indicative of the angle of the head section 350.

The incontinence detection system 80 is positioned either on the bed 300, e.g., as an incontinence detection pad 90, or on the occupant, e.g., as a diaper 100. The incontinence detection system 80 communicates with the controller 302 and sends signals to the controller 302 indicative of an incontinence event. Likewise, a movement monitor 360 detects when the occupant has exited the bed 300. The movement monitor 360 sends signals to the controller 302 indicative of bed exit detection.

A cart sensor 370 is provided to detect when a food cart (not shown) has its base positioned under the apparatus 10. For example, most food carts are made from metal. In such an embodiment, the sensor 370 may include an inductor or capacitor that detects the presence of metal under the apparatus 10. In another embodiment, the sensor 370 may include an RFID tag reader that reads a corresponding RFID tag on the food cart. The sensor 370 is configured to transmit signals to the controller 302 indicative of the presence of the food cart.

The vital signs monitor 280 may also be positioned near the bed 300 and coupled to the occupant. The vital signs monitor 280 monitors vital signs of the occupant, e.g. heartrate, blood pressure, respiratory rate, or the like. In some embodiments, the vital signs monitor 280 may be at least one of a heart rate monitor, a respiration rate monitor, a blood pressure monitor, a temperature monitor, or a pulse oximeter. The vital signs monitor 280 communicates with the controller 302 to send signals to the controller 302 indicative of a vital sign of the occupant.

Figure 6:
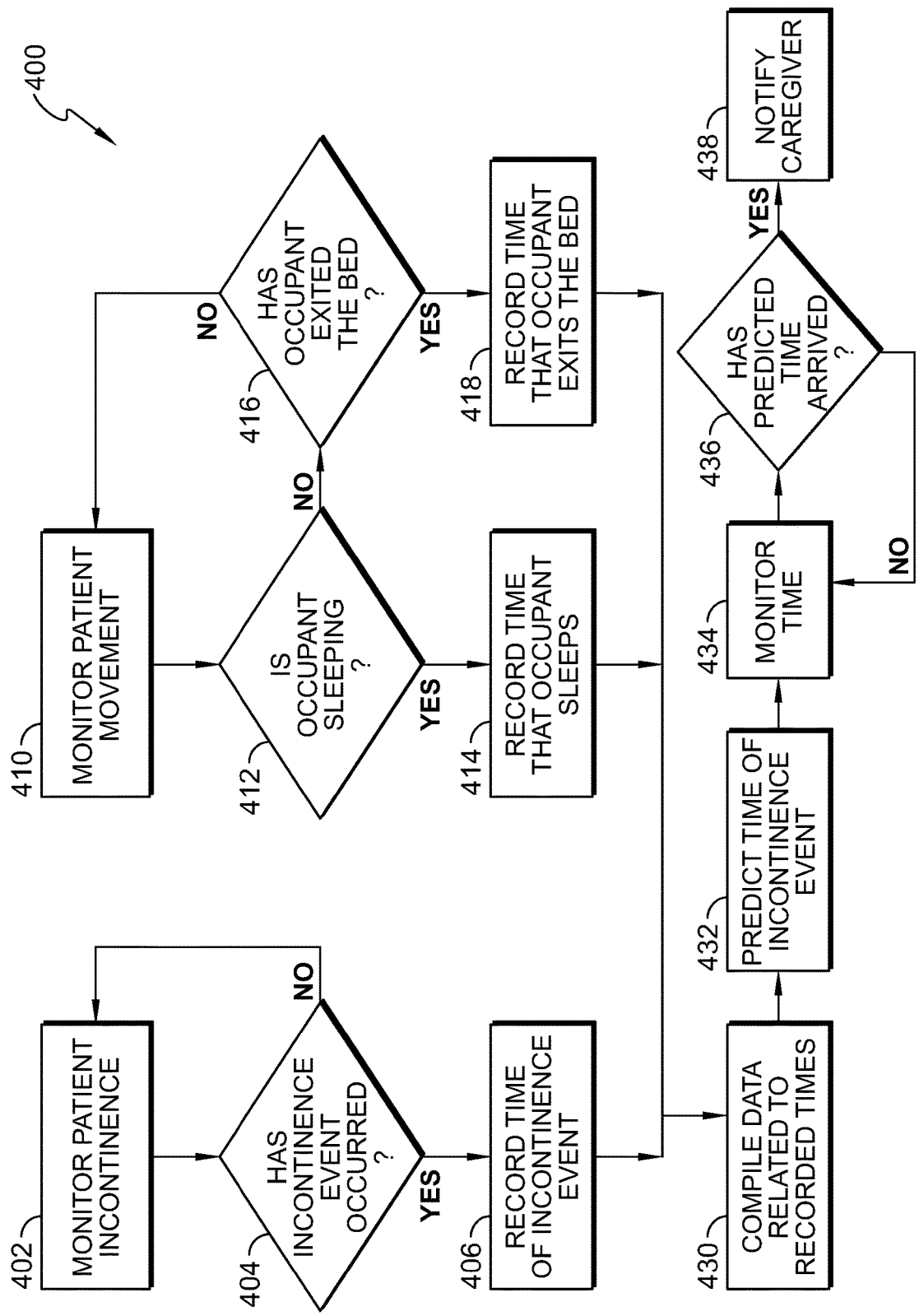
FIG. 6 is a flow chart illustrating an algorithm that executes a routine for alerting a caregiver of future occupant incontinence.

FIGS. 6-12 illustrate various routines for detecting future incontinence events in either the apparatus 10 or the bed 300. For the sake of simplicity, the routines will be described as related to the apparatus 10, shown in FIGS. 1 and 4; however, it should be noted that these routines are equally applicable to the bed 300, shown in FIG. 5. Referring now to FIG. 6, a routine 400 for predicting future incontinence events includes the process step 402 of monitoring occupant incontinence. For example, occupant incontinence may be detected using the incontinence detection system 80. At decision step 404, the controller 32 determines whether occupant incontinence has occurred based on signals from the incontinence detection system 80. If occupant incontinence has not occurred, the controller 32 continues to monitor for incontinence at process step 402. If the incontinence detection system 80 sends a signal to the controller 32 that incontinence as occurred, the controller 32 records the time of the incontinence event, at process step 406.

While incontinence is monitored, the movement monitor 40 also monitors for occupant movement, at process step 410. At decision step 412, the movement monitor 40 determines whether the occupant is sleeping. For example, a lack of movement over an extended period of time may be indicative of the occupant sleeping. If the occupant is determined to be sleeping, the controller 32 records a time that the occupant has slept, at process step 414. If the occupant is determined to not be sleeping, the movement monitor 40 determines whether the occupant has exited the apparatus 10, at process step 416. For example, if the movement monitor 40 fails to record any pressure on the mattress 18, such lack of pressure is likely indicative of the occupant having exited the apparatus 10. Further, a shift in weight to one side of the mattress 18, may also be indicative that the occupant is about the exit the corresponding side of the apparatus 10. If the movement monitor 40 determines that the occupant is not exiting the apparatus 10, the movement monitor 40 continues to monitor occupant movement, at process step 410. If the movement monitor 40 determines that the occupant has exited the apparatus 10, the controller 32 records the time that the occupant exited the apparatus 10, at process step 418.

At process step 430, the controller 32 compiles the data related to each of the recorded times. That is, the data related to the time of incontinence events, the time of sleeping, and the time of exiting the bed is compiled. At process step 432, the controller 32 predicts a time of a future incontinence event. For example, if the occupant either has an incontinence event within 15 minutes of waking each morning or the occupant exits the bed within 15 minutes of waking each morning, presumably to use the toilet, the controller 32 can predict that an incontinence event will occur within 15 minutes of the movement monitor 40 detecting that the occupant has awoken. In another example, the controller 32 may compile data that indicates that an incontinence event or bed exit event occurs every day between 9:00 AM and 9:15 AM. Accordingly, the controller 32 may predict a future incontinence event between 9:00 AM and 9:15 AM. In some embodiments, the controller 32 may notify the caregiver that an incontinence is likely to occur within a particular time frame, e.g. in the next 15-30 minutes. In some embodiments, the recorded times are compiled and correlated within other data, as described herein, to predict the future incontinence event. For example, the recorded times may be correlated with at least one of feeding data, lateral rotation data, head angle data, vital sign data, or the like.

At process step 434, the controller 32 monitors the time. At decision step 436, the controller 32 determines whether the predicted time has arrived. In some embodiments, the controller 32 may determine whether the actual time is within a predetermined time frame from the predicted time, for example, within five minutes of the predicted time. If the predicted time has not arrived, the controller 32 continues to monitor the time, at process step 434. If the predicted time has arrived, the controller 32, notifies the caregiver, at process step 438. For example, the caregiver may be notified on the display 210 of the controller 32. In another example, the caregiver may be notified on the display 228 of the remote device 220.

Accordingly, in one example, if the occupant regularly becomes incontinent within 15 minutes of waking up, the movement monitor 40 will detect that the occupant has woken up and the controller 32 will set an alarm for a predicted future incontinence event within 15 minutes. At the time of the predicted future incontinence event (or a predetermined period of time before), the caregiver will be alerted that the occupant requires assistance with using the toilet. In another example, if the occupant is incontinent every day between 9:00 AM and 9:15 AM, the controller 32 will proactively set an alert for 9:00 AM (or a predetermined period of time before). The caregiver is then alerted to the occupants need for toileting before the incontinence event occurs.

Figure 7:
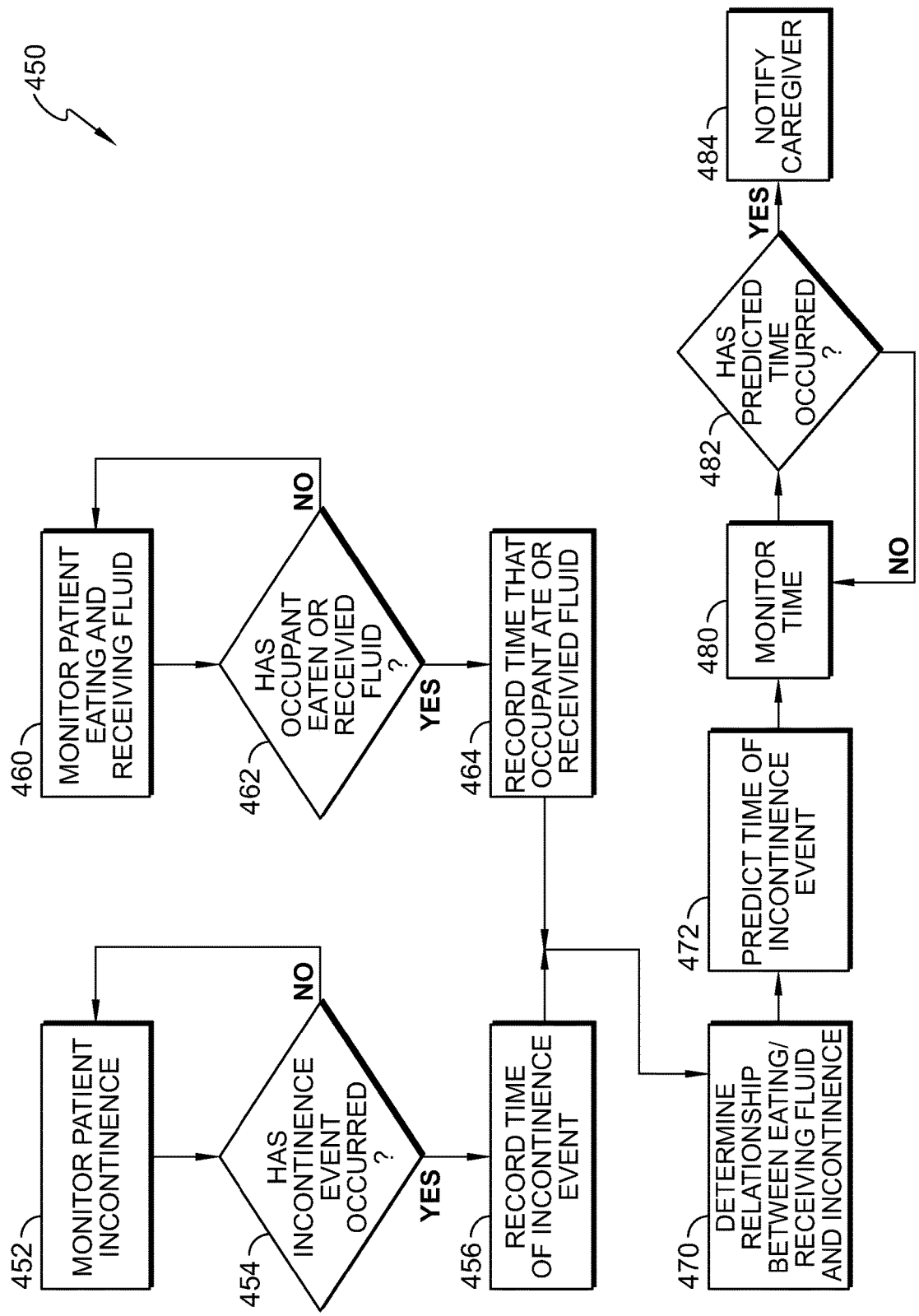
FIG. 7 is a flow chart illustrating another algorithm that executes a routine for alerting a caregiver of future occupant incontinence.

Referring to FIG. 7, another routine 450 for predicting future incontinence events includes monitoring for occupant incontinence, at process step 452. At decision step 454, the controller 32 determines whether occupant incontinence has occurred based on signals from the incontinence detection system 80. If occupant incontinence has not occurred, the controller 32 continues to monitor for incontinence at process step 452. If the incontinence detection system 80 sends a signal to the controller 32 that incontinence as occurred, the controller 32 records the time of the incontinence event, at process step 456.

At the same time, the controller 32 tracks when the occupant eats and receives fluids, e.g. receives a drink or an intravenous fluid, at process step 460. At decision step 462, the controller determines whether the occupant has eaten or received fluid. For example, each time the occupant is fed or given a drink, the caregiver may input the time into the user input 212 of the controller 32. In another embodiment, each time the occupant is fed or given a drink, the caregiver may input the time into the user input 230 of the remote device 220. In yet another embodiment, the controller 32 may determine that the occupant is being fed when the cart sensor 270 detects a base of a food cart is positioned under the apparatus 10. In another embodiment, the occupant may input the time into the user input 230. If the occupant is not being fed, the controller 32 continues to track when the occupant eats and receives fluid, at process step 460. If the controller 32 detects that the occupant has been fed or given fluid, the controller records the time of feeding, at process step 464.

At process step 470, the controller 32 determines a relationship between the occupant eating/receiving fluid and occupant incontinence. At process step 472, the controller 32 predicts a time of a future incontinence event based on the relationship between eating/receiving fluid and occupant incontinence. In other embodiments, additional data, for example, the data described herein, may also be considered when predicting the time of a future incontinence event. For example, the feeding data may be correlated with at least one of movement data, lateral rotation data, head angle data, vital sign data, or the like. At process step 480, the controller 32 monitors the time and, at decision step 482, the controller 32 determines whether the predicted time has arrived. If the predicted time has not arrived, the controller 32 continues to monitor the time, at process step 480. If the predicted time has arrived, the controller 32 alerts the caregiver that an incontinence event is likely to occur, at process step 484.

In one example, if an incontinence event regularly occurs 30 minutes after the occupant is fed, the controller 32 may predict an incontinence event 30 minutes after each feeding. That is, if the occupant is fed at 3:00 PM, the controller 32 predicts an incontinence event at 3:30 PM. Then, at 3:30 PM (or a predetermined time before), the caregiver is notified that the occupant is in need of assistance with toileting. In some embodiments, the controller 32 may notify the caregiver that an incontinence is likely to occur within a particular time frame, e.g. in the next 15-30 minutes.

Figure 8:
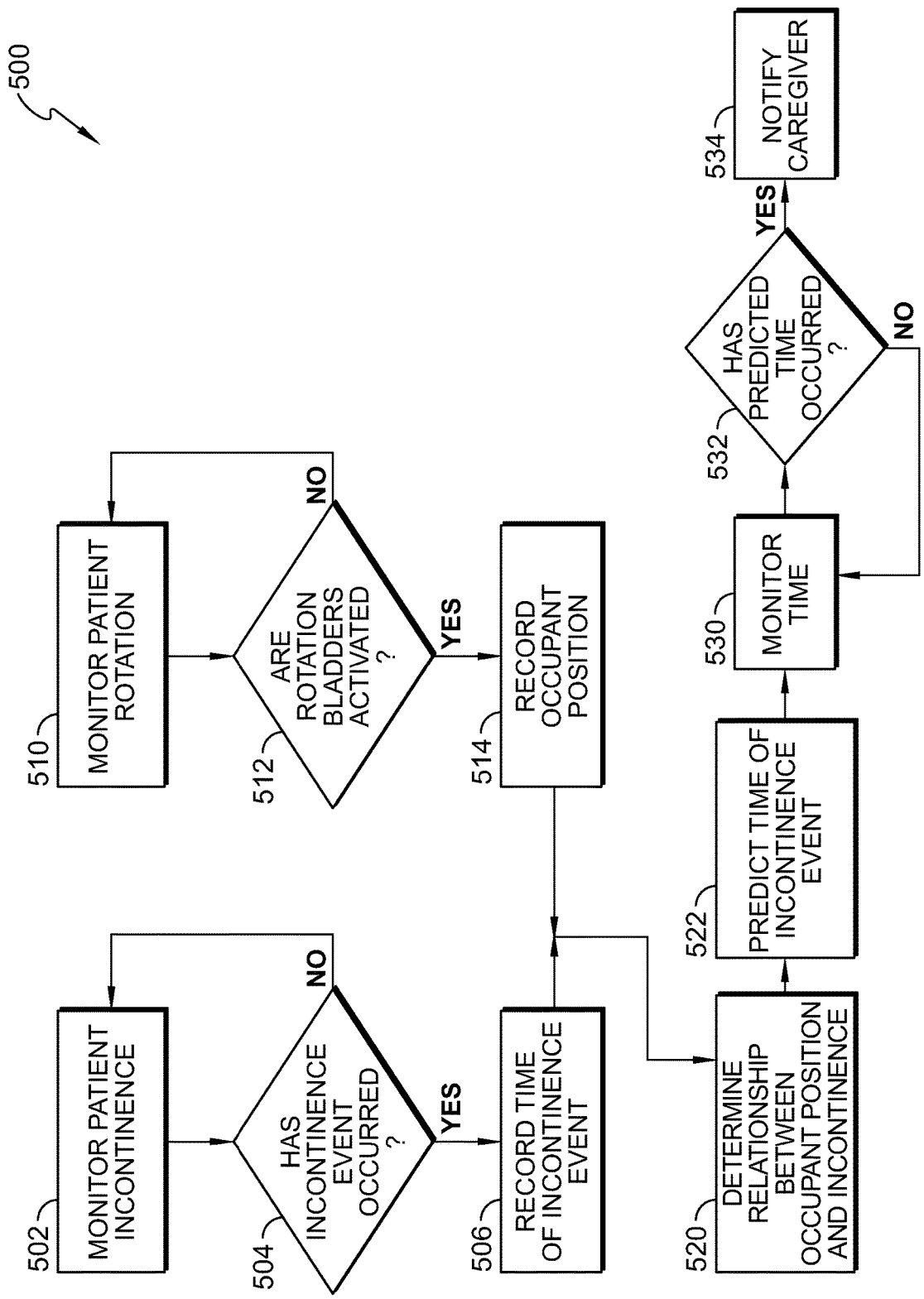
FIG. 8 is a flow chart illustrating yet another algorithm that executes a routine for alerting a caregiver of future occupant incontinence.

Referring now to FIG. 8, another routine 500 for predicting future incontinence events includes monitoring for occupant incontinence, at process step 502. At decision step 504, the controller 32 determines whether occupant incontinence has occurred based on signals from the incontinence detection system 80. If occupant incontinence has not occurred, the controller 32 continues to monitor for incontinence at process step 502. If the incontinence detection system 80 sends a signal to the controller 32 that incontinence as occurred, the controller 32 records the time of the incontinence event, at process step 506.

At the same time, the controller 32 monitors lateral rotation angle data from the rotational angle sensors 70, at process step 510. At decision step 512, the controller 32 determines whether any of the bladders 50 have been activated, e.g., inflated or deflated. If the bladders 50 have not been activated, the controller 32 continues to monitor the lateral rotation angle, at process step 510. If the bladders 50 have been activated, the controller 32 records an occupant position, at process step 514. For example, the controller 32 may record that the occupant is at a right turn angle or a left turn angle.

At process step 520, the controller 32 correlates the occupant position and the incontinence event data and, at process step 522, the controller predicts a future incontinence event. In some embodiments, the data is correlated with other data described herein, for example movement data, feeding data, head angle data, or vital sign data. For example, is the occupant is more likely to have an incontinent event while positioned at a right turn angle for over 20 minutes, the controller 32 may determine the a future incontinence event will occur 20 minutes after the occupant is positioned at a right turn angle. At process step 530, the controller monitors the time and, at decision step 532, the controller 32 determines whether the predicted time has occurred (or will occur within a predetermined period of time). If the predicted time has not occurred, the controller 32 continues to monitor the time, at process step 530. If the predicted time has occurred, the controller 32 notifies a caregiver that an incontinence event is likely to occur, at process step 534. For example, if the occupant has been at a right turn angle for over 15 minutes, the controller 32 notifies the caregiver of the predicted future incontinence event. In some embodiments, the controller 32 may notify the caregiver that an incontinence is likely to occur within a particular time frame, e.g. in the next 15-30 minutes.

Figure 9:
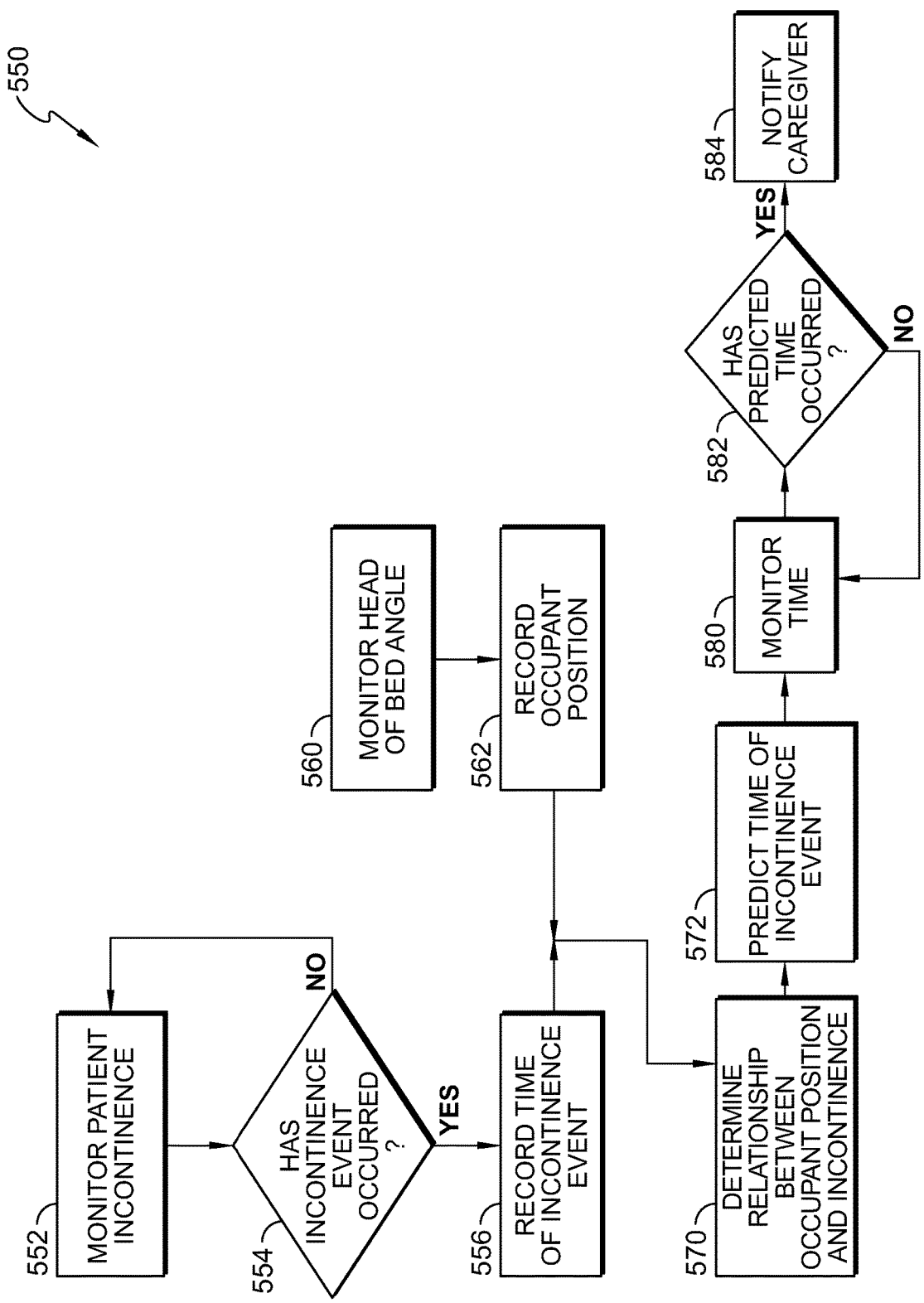
FIG. 9 is a flow chart illustrating a further another algorithm that executes a routine for alerting a caregiver of future occupant incontinence.

Referring to FIG. 9, another routine 550 for predicting future incontinence events includes monitoring for occupant incontinence, at process step 552. At decision step 554, the controller 32 determines whether occupant incontinence has occurred based on signals from the incontinence detection system 80. If occupant incontinence has not occurred, the controller 32 continues to monitor for incontinence at process step 552. If the incontinence detection system 80 sends a signal to the controller 32 that incontinence as occurred, the controller 32 records the time of the incontinence event, at process step 556.

At the same time, the controller 32 monitors head section angle data from the head angle sensor 34, at process step 560. At process step 562, record the head angle of the head section 16. At process step 570, the controller 32 correlates the occupant position, e.g., the head angle, and the incontinence event data and, at process step 572, the controller predicts a future incontinence event. In some embodiments, the data is correlated with other data described herein, for example movement data, feeding data, lateral rotation angle data, or vital sign data. For example, is the occupant is more likely to have an incontinent event while positioned at a 30 degree angle for over 20 minutes, the controller 32 may determine the a future incontinence event will occur 20 minutes after the occupant is positioned at a 30 degree angle. At process step 580, the controller monitors the time and, at decision step 582, the controller 32 determines whether the predicted time has occurred (or will occur within a predetermined period of time). If the predicted time has not occurred, the controller 32 continues to monitor the time, at process step 580. If the predicted time has occurred, the controller 32 notifies a caregiver that an incontinence event is likely to occur, at process step 584. For example, if the occupant has been at a head section angle of 30 degrees for over 15 minutes, the controller 32 notifies the caregiver of the predicted future incontinence event. In some embodiments, the controller 32 may notify the caregiver that an incontinence is likely to occur within a particular time frame, e.g. in the next 15-30 minutes.

Figure 10:
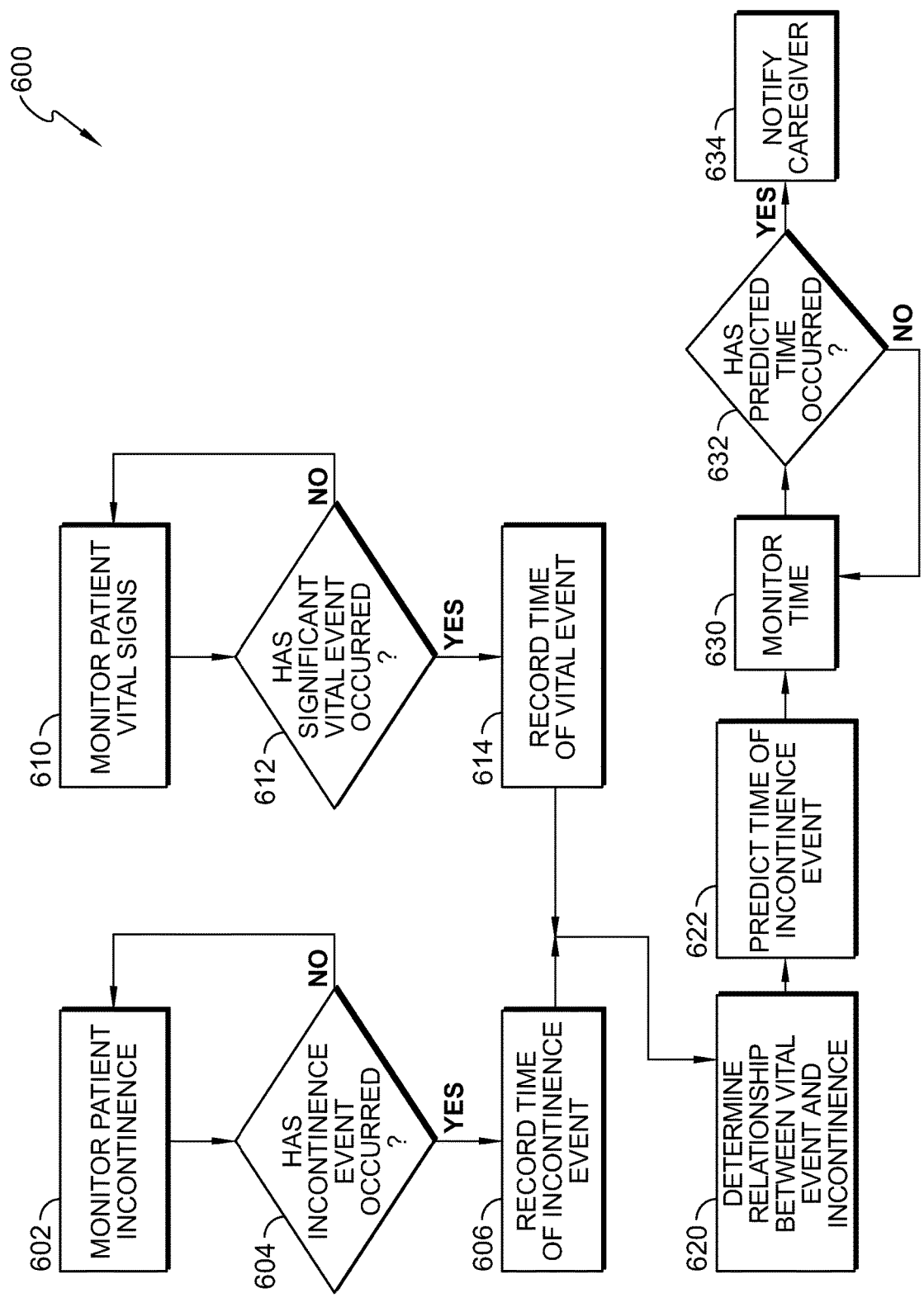
FIG. 10 is a flow chart illustrating an another embodiment of an algorithm that executes a routine for alerting a caregiver of future occupant incontinence.

Referring now to FIG. 10, another routine 600 for predicting future incontinence events includes monitoring for occupant incontinence, at process step 602. At decision step 604, the controller 32 determines whether occupant incontinence has occurred based on signals from the incontinence detection system 80. If occupant incontinence has not occurred, the controller 32 continues to monitor for incontinence at process step 602. If the incontinence detection system 80 sends a signal to the controller 32 that incontinence as occurred, the controller 32 records the time of the incontinence event, at process step 606.

At the same time, the controller 32 monitors occupant vital signs with the vital sign monitor 280, at process step 610. At decision step 612, the controller 32 determines whether a vital sign event has occurred. For example, the controller 32 may determine that the occupant is experiencing an increased heartrate. If a vital sign event has not occurred, the controller 32 continues to monitor the occupant vital signs, at process step 610. If a vital sign event has occurred, the controller 32 records a time of the event, at process step 614. For example, the controller 32 may record a time that the occupant experiences an increased heartrate.

At process step 620, the controller 32 correlates the vital sign data and the incontinence event data and, at process step 622, the controller predicts a future incontinence event. In some embodiments, the data is correlated with other data described herein, for example movement data, feeding data, lateral rotation data, head angle data. For example, is the occupant is more likely to have an incontinent event while they are experiencing an increased heartrate, the controller 32 may determine the a future incontinence event will occur 10 minutes after the occupant experiences the increased heartrate. At process step 630, the controller monitors the time and, at decision step 632, the controller 32 determines whether the predicted time has occurred (or will occur within a predetermined period of time). If the predicted time has not occurred, the controller 32 continues to monitor the time, at process step 630. If the predicted time has occurred, the controller 32 notifies a caregiver that an incontinence event is likely to occur, at process step 634. For example, if the occupant has experienced an increased heartrate for 10 minutes, the controller 32 notifies the caregiver of the predicted future incontinence event. In some embodiments, the controller 32 may notify the caregiver that an incontinence is likely to occur within a particular time frame, e.g. in the next 15-30 minutes.

Figure 11:
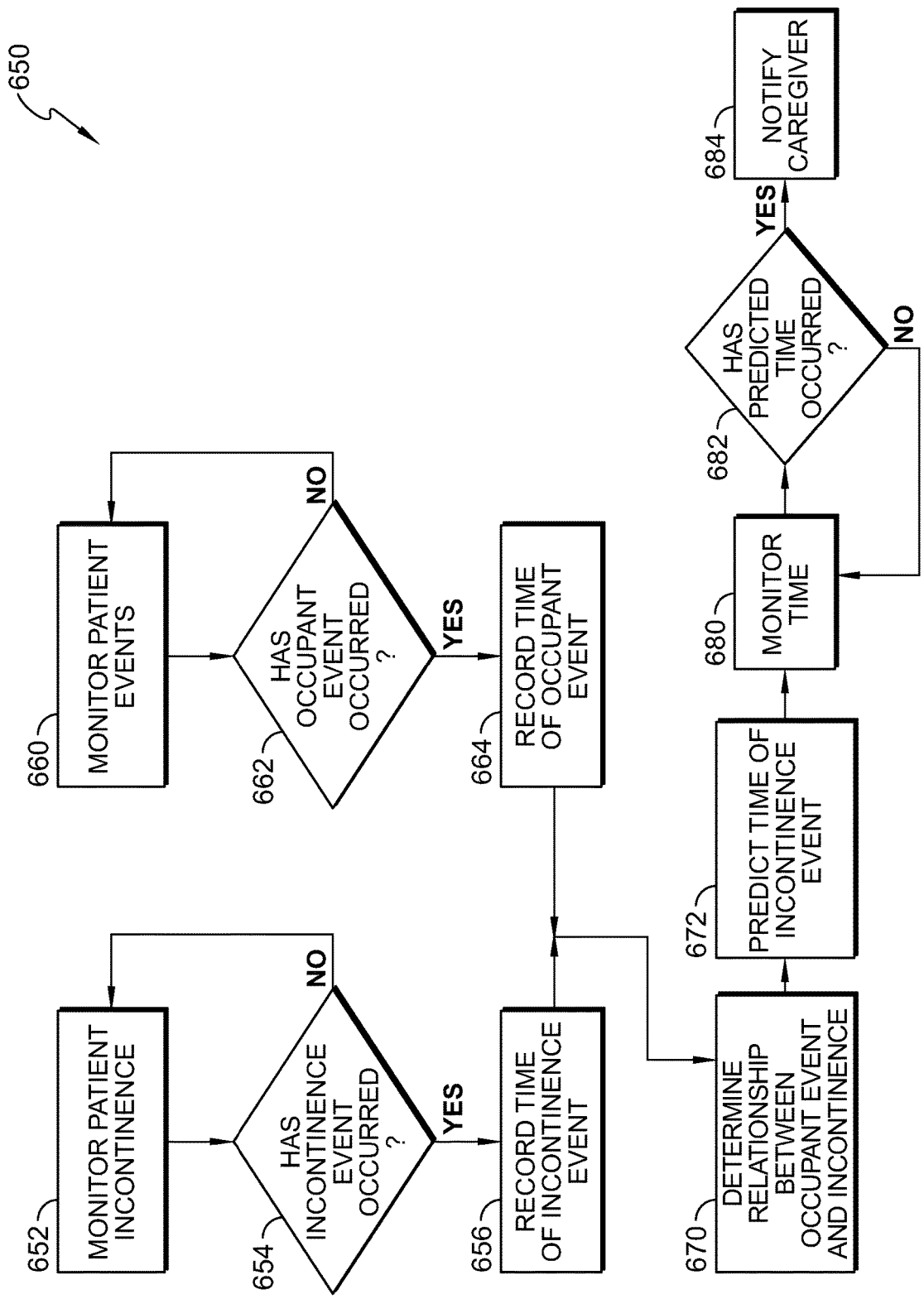
FIG. 11 is a flow chart illustrating yet another algorithm that executes a routine for alerting a caregiver of future occupant incontinence.

Referring now to FIG. 11, another routine 650 for predicting future incontinence events includes monitoring for occupant incontinence, at process step 652. At decision step 654, the controller 32 determines whether occupant incontinence has occurred based on signals from the incontinence detection system 80. If occupant incontinence has not occurred, the controller 32 continues to monitor for incontinence at process step 652. If the incontinence detection system 80 sends a signal to the controller 32 that incontinence as occurred, the controller 32 records the time of the incontinence event, at process step 656.

At the same time, the controller 32 monitors occupant events with any of a plurality of known sensors or monitors, at process step 660. At decision step 662, the controller 32 determines whether an occupant event has occurred. If an occupant event has not occurred, the controller 32 continues to monitor for occupant events, at process step 662. If an occupant event has occurred, the controller 32 records a time of the event, at process step 664.

At process step 670, the controller 32 correlates the occupant event data and the incontinence event data and, at process step 672, the controller predicts a future incontinence event. For example, is the occupant is more likely to have an incontinent event within 20 minutes of an occupant event, the controller 32 may determine the a future incontinence event will occur 20 minutes after the next occupant event. At process step 680, the controller monitors the time and, at decision step 682, the controller 32 determines whether the predicted time has occurred (or will occur within a predetermined period of time). If the predicted time has not occurred, the controller 32 continues to monitor the time, at process step 680. If the predicted time has occurred, the controller 32 notifies a caregiver that an incontinence event is likely to occur, at process step 684. For example, if the occupant has experienced an occupant event, the controller 32 notifies the caregiver of the predicted future incontinence event within 20 minutes. In some embodiments, the controller 32 may notify the caregiver that an incontinence is likely to occur within a particular time frame, e.g. in the next 15-30 minutes.

Figure 12:
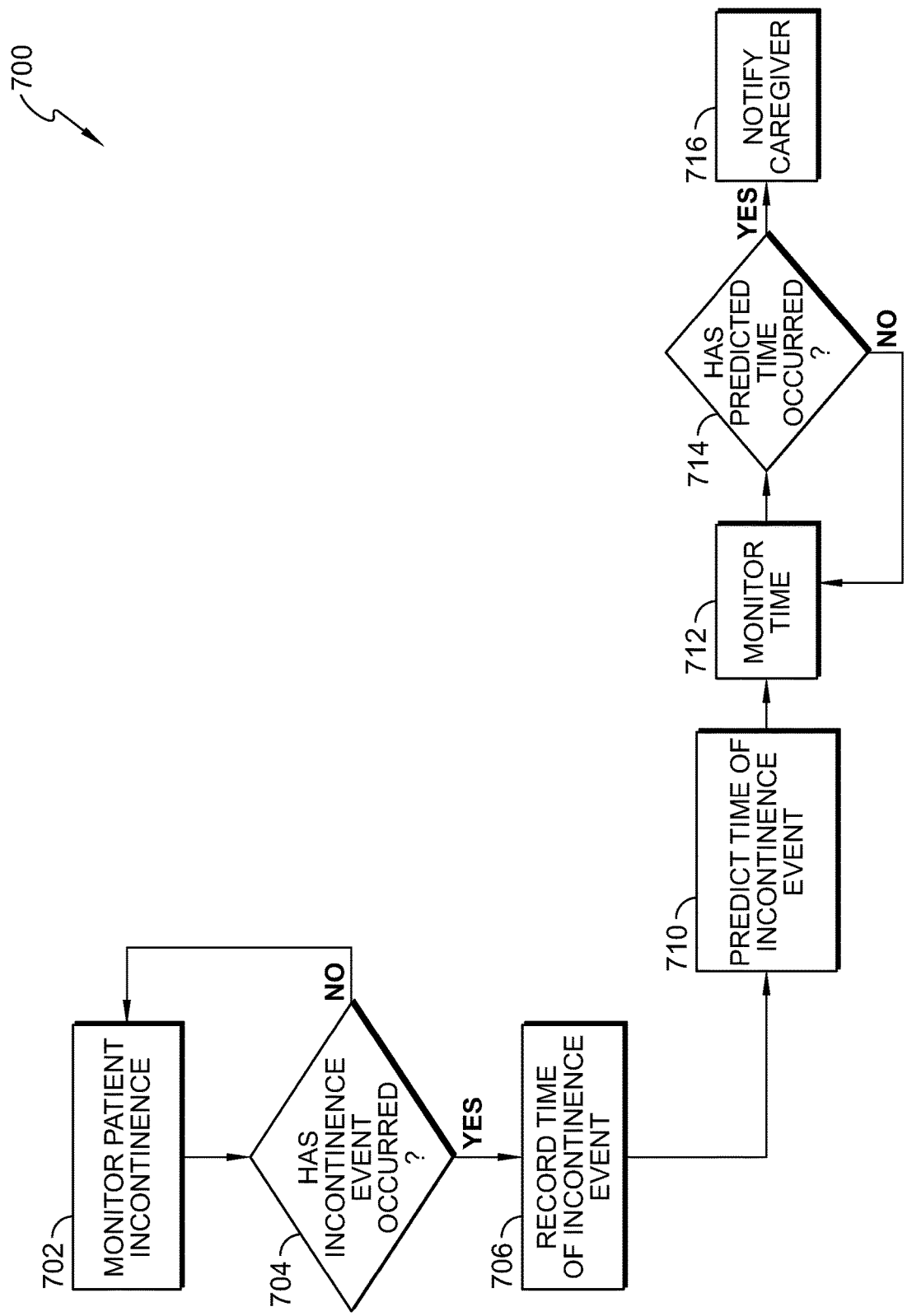
FIG. 12 is a flow chart illustrating a further another algorithm that executes a routine for alerting a caregiver of future occupant incontinence.

Referring to FIG. 12, another routine 700 for predicting future incontinence events includes monitoring for occupant incontinence, at process step 702. At decision step 704, the controller 32 determines whether occupant incontinence has occurred based on signals from the incontinence detection system 80. If occupant incontinence has not occurred, the controller 32 continues to monitor for incontinence at process step 702. If the incontinence detection system 80 sends a signal to the controller 32 that incontinence as occurred, the controller 32 records the time of the incontinence event, at process step 706.

At process step 710, the controller 32 predicts a time of a future incontinence event. For example, if the occupant is regularly incontinent at noon, the controller 32 predicts that an incontinent event will occur each day between 11:45 AM and 12:15 PM. The data related to the time of incontinence events may also be correlated with other data as described herein. At process step 712, the controller monitors the time and, at decision step 714, the controller 32 determines whether the predicted time has occurred (or will occur within a predetermined period of time). If the predicted time has not occurred, the controller 32 continues to monitor the time, at process step 712. If the predicted time has occurred, the controller 32 notifies a caregiver that an incontinence event is likely to occur, at process step 716. For example, the controller 32 may notify the caregiver of the predicted future incontinence event at 11:45 AM. In some embodiments, the controller 32 may notify the caregiver that an incontinence is likely to occur within a particular time frame, e.g. in the next 15-30 minutes.

The present disclosure contemplates embodiments in which one or more of routines 400, 450, 500, 550, 600, 650, 700 of FIGS. 6-12, respectively, are executed concurrently or serially. Thus, some embodiments execute only one of routines 400, 450, 500, 550, 600, 650, 700. Other embodiments execute any two of routines 400, 450, 500, 550, 600, 650, 700. Further embodiments execute any three of routines 400, 450, 500, 550, 600, 650, 700. Still other embodiments execute any four of routines 400, 450, 500, 550, 600, 650, 700. Still further embodiments execute any five of routines 400, 450, 500, 550, 600, 650, 700. Yet other embodiments execute any six of routines 400, 450, 500, 550, 600, 650, 700. Yet further embodiments execute all seven of routines 400, 450, 500, 550, 600, 650, 700.

Although this disclosure refers to specific embodiments, it will be understood by those skilled in the art that various changes in form and detail may be made without departing from the subject matter set forth in the accompanying claims.

The invention claimed is:

1. An incontinence detection alert system comprising:
    a bed having a patient support surface configured to receive an occupant;
    at least one monitor configured to acquire data related to at least one of a status of the bed or a status of the occupant, wherein the at least one monitor includes a movement detection system positioned under the patient support surface and configured to determine when the occupant has exited the bed;
    an incontinence detection system having circuitry to detect an incontinence event of the occupant;
    a controller configured to receive the data from the at least one monitor, the controller configured to further receive data related to a time of the incontinence event, the controller determining a predicted future incontinence event based on the data from the at least one monitor and the data related to the time of the incontinence event, wherein the controller correlates a time that the occupant exits the bed and the time of the incontinence event to determine a plurality of times that the occupant has required toileting; and
    a remote device configured to receive an alert from the controller before the predicted time of the future incontinence event.

2. The system of claim 1, wherein the controller includes a transceiver to transmit outgoing signals to the remote device and to receive incoming signals from the remote device.

3. The system of claim 1, wherein the remote device is a remote computer.

4. The system of claim 1, wherein the remote device is a mobile device of a caregiver.

5. The system of claim 1, wherein the remote device receives the alert from the controller at least five minutes before the predicted time.

6. The system of claim 1, wherein the plurality of times that the occupant has required toileting is correlated to the predicted time of the future incontinence event.

7. The system of claim 1, wherein the at least one monitor includes a memory that stores a time that the occupant receives at least one of food and fluids.

8. The system of claim 7, further comprising a cart sensor configured to detect when a food cart is positioned under the bed.

9. The system of claim 7, wherein the controller includes at least one input, wherein the time that the occupant receives at least one of food and fluids is stored into the memory using the at least one input of the controller.

10. The system of claim 7, wherein the remote device includes at least one input, wherein the time that the occupant receives at least one of food and fluids is stored into the memory using the at least one input of the remote device.

11. The system of claim 7, wherein the controller compares the time that the occupant receives at least one of food and fluids to the time of the incontinence event to determine a time lapse between the time that the occupant receives at least one of food and fluids and the time of the incontinence event.

12. The system of claim 11, wherein the predicted time of the future incontinence event is determined based on the time lapse between the time that the occupant receives at least one of food and fluids and the time of the incontinence event.

13. The system of claim 1, wherein the at least one monitor includes an angle sensor that determines a rotational angle of a mattress on the bed.

14. The system of claim 13, wherein the controller determines a rotational angle of the mattress at the time of the incontinence event to determine a correlation between an occupant position and the time of the incontinence event.

15. The system of claim 14, wherein the controller determines the predicted time of the future incontinence event based on the correlation between the occupant position and the time of the incontinence event.

16. The system of claim 1, wherein the at least one monitor includes an angle sensor that determines an angle of a head section of the bed.

17. The system of claim 16, wherein the controller determines the angle of the head section at the time of the incontinence event to determine a correlation between an occupant position and the time of the incontinence event.

18. The system of claim 17, wherein the controller determines the predicted time of the future incontinence event based on the correlation between the occupant position and the time of the incontinence event.

19. The system of claim 1, wherein the at least one monitor includes a vital sign monitor.

20. The system of claim 19, wherein the controller compares data from the vital sign monitor to the time of the incontinence event to determine a correlation between a vital sign of the occupant and the time of the incontinence event.

21. The system of claim 20, wherein the controller determines the predicted time of the future incontinence event based on the correlation between the vital sign of the occupant and the time of the incontinence event.

* * * * *